(12) United States Patent
Rubin et al.

(10) Patent No.: US 7,658,724 B2
(45) Date of Patent: Feb. 9, 2010

(54) APPARATUS AND METHOD FOR RAPID AUTO-INJECTION OF MEDICATION

(75) Inventors: Keith H. Rubin, Fort Lauderdale, FL (US); James M. Sellers, Salem, NH (US); Haydn B. Taylor, Nashua, NH (US)

(73) Assignee: Seedings Life Science Ventures LLC, New York, NY (US)

( * ) Notice: Subject to any disclaimer, the term of this patent is extended or adjusted under 35 U.S.C. 154(b) by 744 days.

(21) Appl. No.: 11/089,485

(22) Filed: Mar. 24, 2005

(65) Prior Publication Data

US 2005/0171477 A1    Aug. 4, 2005

Related U.S. Application Data

(62) Division of application No. 10/154,202, filed on May 23, 2002, now Pat. No. 6,979,316.

(51) Int. Cl.
*A61M 5/20* (2006.01)
*A61M 5/00* (2006.01)

(52) U.S. Cl. .................. 604/137; 604/181; 604/110

(58) Field of Classification Search ........... 604/187, 604/197, 195, 156, 131, 134–7, 181, 192–4, 604/232, 110
See application file for complete search history.

(56) References Cited

U.S. PATENT DOCUMENTS

| | | | |
|---|---|---|---|
| 1,288,174 A | 12/1918 | Pittenger et al. |
| 2,408,323 A | 9/1946 | Lockhart et al. |
| 2,576,951 A | 12/1951 | Lockhart |
| 2,589,426 A | 3/1952 | Ogle |
| 2,605,765 A | 8/1952 | Kollsman |
| 2,667,164 A | 1/1954 | Smith |
| 2,667,165 A | 1/1954 | Smith |
| 2,769,443 A | 11/1956 | Dunmire |
| 2,871,856 A | 2/1959 | Steiner et al. |
| 2,880,723 A | 4/1959 | Adams |
| 3,082,681 A | 3/1963 | Petersen |
| 3,238,784 A | 3/1966 | Dorsey et al. |
| 3,306,290 A | 2/1967 | Weltman |
| 3,391,695 A | 7/1968 | Sarnoff |

(Continued)

FOREIGN PATENT DOCUMENTS

EP    0258073    3/1988

(Continued)

*Primary Examiner*—Kevin C Sirmons
*Assistant Examiner*—Catherine N Witczak
(74) *Attorney, Agent, or Firm*—K&L Gates LLP

(57) ABSTRACT

An auto-injector for rapid delivery of a bolus of injectable medication has a generally flat, sealed housing with small peripheral dimensions, approximating those of a credit card. A syringe, configured to be contained within the flat housing is pre-filled with the medication. The housing contains a mechanism that, when triggered, automatically drives the syringe and needle forwardly to an injection position and then continues to compress the volume of the syringe to effect rapid injection. The forward injection end of the device includes an actuator that also conceals and protects the needle at all times and, prevents post-injection hazards. The flat faces of the device have graphic symbols and other visual indicia relating to the operation and condition of the device. The device enables a simple three-step operation that reduces the risk of improper use.

5 Claims, 25 Drawing Sheets

U.S. PATENT DOCUMENTS

| | | |
|---|---|---|
| 3,469,578 A | 9/1969 | Bierman |
| 3,496,937 A | 2/1970 | Balson |
| 3,506,005 A | 4/1970 | Gilio et al. |
| 3,507,278 A | 4/1970 | Werding |
| 3,563,373 A | 2/1971 | Paulson |
| 3,587,575 A | 6/1971 | Lichtenstein |
| 3,677,444 A | 7/1972 | Merrill |
| 3,702,609 A | 11/1972 | Steiner |
| 3,712,301 A | 1/1973 | Sarnoff |
| 3,882,863 A | 5/1975 | Sarnoff et al. |
| 3,941,131 A | 3/1976 | Ogle |
| 4,013,073 A | 3/1977 | Cunningham |
| 4,031,893 A | 6/1977 | Kaplan et al. |
| 4,044,758 A | 8/1977 | Patel |
| 4,188,950 A | 2/1980 | Wardlaw |
| 4,193,397 A | 3/1980 | Tucker et al. |
| 4,194,505 A | 3/1980 | Schmitz |
| 4,196,732 A | 4/1980 | Wardlaw |
| 4,201,207 A | 5/1980 | Buckles et al. |
| 4,214,584 A | 7/1980 | Smirnov et al. |
| 4,227,528 A | 10/1980 | Wardlaw |
| 4,258,713 A | 3/1981 | Wardlaw |
| 4,270,533 A | 6/1981 | Andreas |
| 4,282,986 A | 8/1981 | Ekenstam et al. |
| 4,340,048 A | 7/1982 | Eckenhoff |
| 4,373,527 A | 2/1983 | Fischell |
| 4,378,015 A | 3/1983 | Wardlaw |
| 4,386,929 A | 6/1983 | Peery et al. |
| 4,419,096 A | 12/1983 | Leeper et al. |
| 4,548,601 A | 10/1985 | Lary |
| 4,553,962 A | 11/1985 | Brunet |
| 4,619,652 A | 10/1986 | Eckenhoff et al. |
| 4,645,495 A | 2/1987 | Vaillancourt |
| 4,692,151 A | 9/1987 | Blackman |
| 4,728,320 A | 3/1988 | Chen et al. |
| 4,734,092 A | 3/1988 | Millerd |
| 4,741,733 A | 5/1988 | Winchell et al. |
| 4,747,831 A | 5/1988 | Kulli |
| 4,753,651 A | 6/1988 | Eckenhoff |
| 4,767,413 A | 8/1988 | Haber |
| 4,769,008 A | 9/1988 | Hessel |
| 4,772,263 A | 9/1988 | Dorman |
| 4,781,688 A | 11/1988 | Thomas et al. |
| 4,813,426 A | 3/1989 | Haber et al. |
| 4,850,961 A | 7/1989 | Wanderer |
| 4,883,473 A | 11/1989 | Thomas |
| 4,886,499 A | 12/1989 | Cirelli et al. |
| 4,894,054 A | 1/1990 | Miskinyar |
| 4,900,310 A | 2/1990 | Ogle |
| 4,909,790 A | 3/1990 | Tsujikawa et al. |
| 4,955,871 A | 9/1990 | Thomas |
| 4,994,042 A | 2/1991 | Vadher |
| 5,019,047 A | 5/1991 | Kriesel |
| 5,019,048 A | 5/1991 | Margolin |
| 5,061,249 A | 10/1991 | Campbell |
| 5,062,834 A | 11/1991 | Gross et al. |
| 5,080,648 A | 1/1992 | D'Antonio |
| 5,085,641 A | 2/1992 | Sarnoff et al. |
| 5,102,393 A | 4/1992 | Sarnoff et al. |
| 5,122,116 A | 6/1992 | Kriesel et al. |
| 5,167,632 A | 12/1992 | Eid et al. |
| 5,169,389 A | 12/1992 | Kriesel |
| 5,176,643 A | 1/1993 | Kramer et al. |
| 5,201,718 A | 4/1993 | Whisson |
| 5,205,820 A | 4/1993 | Kriesel |
| 5,248,303 A | 9/1993 | Margolin |
| 5,267,963 A | 12/1993 | Bachynsky |
| 5,273,544 A * | 12/1993 | van der Wal ................ 604/134 |
| 5,279,558 A | 1/1994 | Kriesel |
| 5,286,258 A * | 2/1994 | Haber et al. .................. 604/90 |
| 5,318,557 A | 6/1994 | Gross |
| 5,320,609 A | 6/1994 | Haber et al. |
| 5,334,197 A | 8/1994 | Kriesel et al. |
| 5,336,188 A | 8/1994 | Kriesel |
| 5,342,320 A | 8/1994 | Cameron |
| 5,391,151 A | 2/1995 | Wilmot |
| 5,398,851 A | 3/1995 | Sancoff et al. |
| 5,419,771 A | 5/1995 | Kriesel |
| 5,425,722 A | 6/1995 | Whisson |
| 5,451,210 A | 9/1995 | Kramer et al. |
| 5,468,226 A | 11/1995 | Kriesel |
| 5,478,324 A | 12/1995 | Meyer |
| 5,492,533 A | 2/1996 | Kriesel |
| 5,498,245 A | 3/1996 | Whisson |
| 5,527,287 A * | 6/1996 | Miskinyar .................... 604/135 |
| 5,540,664 A | 7/1996 | Wyrick |
| 5,551,849 A | 9/1996 | Christiansen |
| 5,569,192 A | 10/1996 | van der Wall |
| 5,616,132 A | 4/1997 | Newman |
| 5,656,032 A | 8/1997 | Kriesel et al. |
| 5,672,883 A | 9/1997 | Reich |
| 5,674,203 A | 10/1997 | Lewandowski |
| 5,693,018 A | 12/1997 | Kriesel et al. |
| 5,704,520 A | 1/1998 | Gross |
| 5,707,365 A * | 1/1998 | Haber et al. ................. 604/191 |
| 5,709,668 A | 1/1998 | Wacks |
| 5,738,657 A | 4/1998 | Bryant |
| 5,743,879 A | 4/1998 | Kriesel |
| 5,776,103 A | 7/1998 | Kriesel et al. |
| 5,779,676 A | 7/1998 | Kriesel et al. |
| 5,785,688 A | 7/1998 | Joshi et al. |
| 5,820,602 A | 10/1998 | Kovelman et al. |
| 5,865,804 A | 2/1999 | Bachynsky |
| 5,921,966 A | 7/1999 | Bendek et al. |
| 5,957,895 A | 9/1999 | Sage et al. |
| 5,957,896 A | 9/1999 | Bendek |
| 5,984,900 A | 11/1999 | Mikkelsen |
| 6,086,562 A | 7/2000 | Jacobsen et al. |
| 6,102,896 A * | 8/2000 | Roser .......................... 604/218 |
| 6,149,626 A | 11/2000 | Bachynsky et al. |
| 6,159,181 A | 12/2000 | Crossman et al. |
| 6,171,276 B1 | 1/2001 | Lippe et al. |
| 6,210,369 B1 | 4/2001 | Wilmot et al. |
| 6,221,044 B1 | 4/2001 | Greco |
| 6,241,709 B1 | 6/2001 | Bechtold et al. |
| 6,270,479 B1 | 8/2001 | Bergens et al. |
| 6,293,925 B1 | 9/2001 | Safabash |
| 6,319,234 B1 | 11/2001 | Restelli et al. |
| 6,530,900 B1 | 3/2003 | Daily et al. |
| 6,530,904 B1 * | 3/2003 | Edwards et al. .............. 604/197 |
| 6,595,956 B1 | 7/2003 | Gross et al. |
| 6,808,514 B2 * | 10/2004 | Schneider et al. ........... 604/232 |
| 2006/0229556 A1 * | 10/2006 | Pressly et al. ................ 604/110 |

FOREIGN PATENT DOCUMENTS

| | | |
|---|---|---|
| EP | 0388169 | 3/1990 |
| WO | WO89/12473 | 12/1989 |
| WO | WO95/13838 | 5/1995 |
| WO | WO97/10012 | 3/1997 |
| WO | WO97/21457 | 6/1997 |
| WO | WO 01/91837 | 12/2001 |
| WO | WO01/93926 | 12/2001 |
| WO | WO02/32287 | 4/2002 |

* cited by examiner

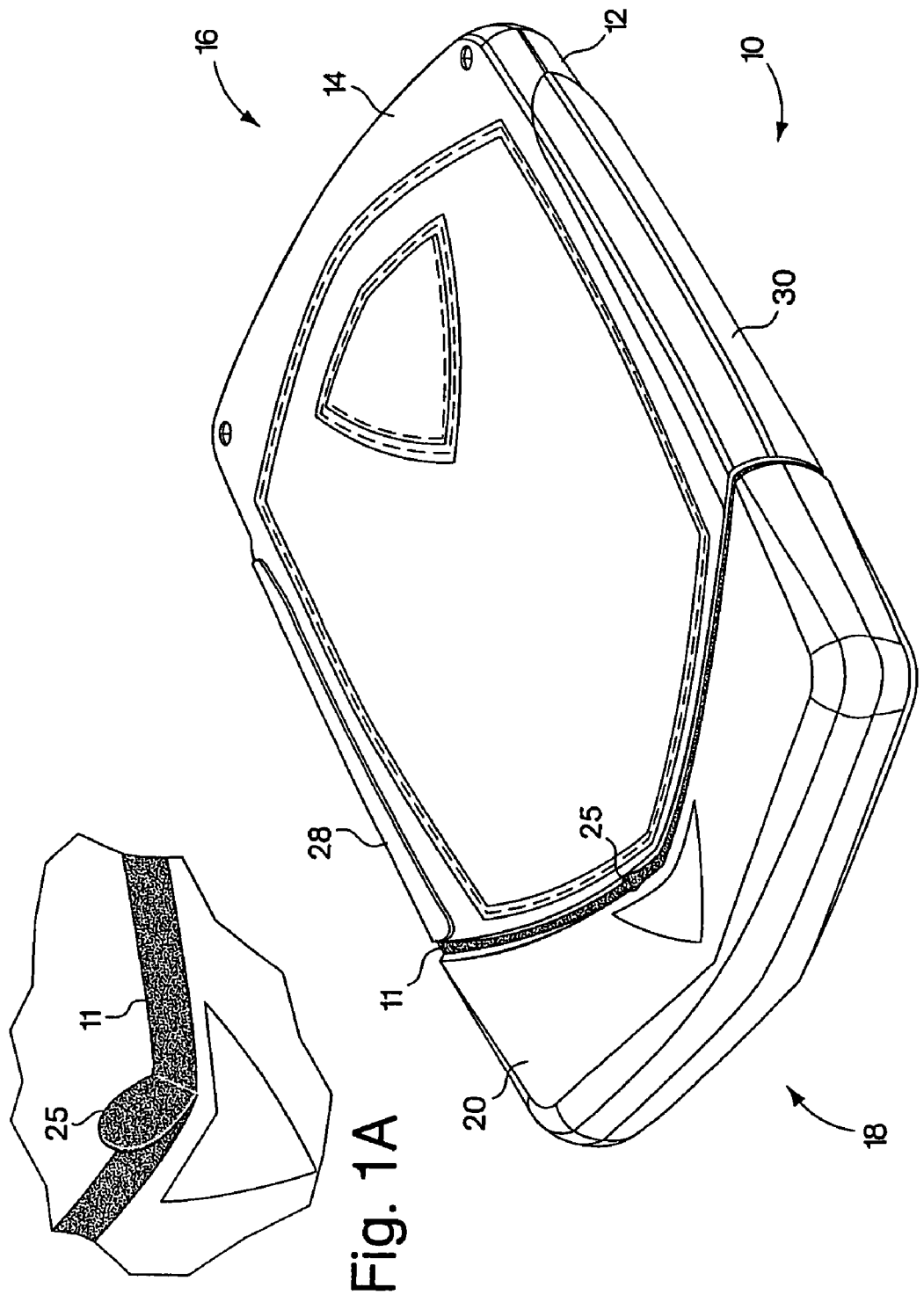

APPARATUS AND METHOD FOR RAPID AUTO-INJECTION OF MEDICATION

RELATED APPLICATION

This application is a divisional of application Ser. No. 10/154,202 filed May 23, 2002.

FIELD

The invention relates to portable auto-injectors for rapid, automatic injection of a measured dose of medication.

BACKGROUND

Certain medical conditions require immediate injection of medication. The condition requiring such treatment may result from a variety of causes. Among the most serious of those conditions is anaphylaxis (a severe allergic reaction) that, in many cases, can become fatal within minutes if left untreated. Among the numerous allergens that may cause anaphylaxis are insect bites, various chemical substances and foods. Food products having even small quantities of peanuts, seafood or milk products can, in some individuals, induce severe, potentially lethal reactions. In foods, the allergen may be "hidden", that is, the food, unknowingly, may contain a minute trace of an allergenic ingredient or may have been exposed to the allergenic ingredient during its processing. When anaphylaxis occurs, often there is insufficient time for the patient to reach a hospital or other trained and equipped medical personnel.

Individuals known to be at risk for anaphylactic reaction typically are advised to carry, at all times, an auto-injection device adapted to inject a bolus of epinephrine. The ability to inject the epinephrine immediately can be a matter of life or death. Notwithstanding the severe risk involved, there is evidence that a large proportion of the population that should be carrying such a device, in fact, does not. At least one study indicates that fewer than 30% of patients at risk of anaphylaxis carry the device at all times. See Goldberg A, Confino-Cohen R., "Insect Sting-Inflicted Systemic Reactions: Attitudes of Patients With Insect Venom Allergy Regarding After-Sting Behavior and Proper Administration of Epinephrine", *J Allergy Clin Immonol* 2000; 106: 1184-9. Food based allergies are reported to cause anaphylactic reactions resulting in 30,000 trips to the emergency room and 150 to 200 deaths per year (www.foodallergy.com). The main factor contributing to a fatal outcome is the fact that the victims did not carry their emergency kit with adrenaline (epinephrine). See Wuthrich, B., "Lethal or Life Threatening Allergic Reactions to Food", *J. Investig Allergol Clin Immunol,* 2000 March-April, 10 (2): 59-65. Moreover, even for those individuals that are required to carry such a device, it has been reported that a large proportion (as much as two-thirds) are insufficiently familiar with its use and operation. See Sicherer, S. H., Forman, J. A., Noone, S. A., "Use Assessment of Self-Administered Epinephrine Among Food-Allergic Children and Pediatricians", *Pediatrics,* 2000; 105: 359-362. Only 25% of physicians, in one study, were able to properly demonstrate the use of the device. See Grouhi, M., Alsherhri, M., Hummel, D, Roifman, C. M., "Anaphylaxis and Epinephrine Auto-injector Training: Who Will Teach the Teachers?, *Journal of Allergy and Clinical Immunology* 1999 July; 104 (1): 190-3. It has been estimated that as many as forty million individuals in the United States are at risk of anaphylaxis. See Neugut, A. I., Ghatak, A. T., and Miller, R. L., "Anaphylaxis in the United States: An Investigation into its Epidemiology", Archives of Internal Medicine 2001 Jan. 8; 161 (1): 15-21.

Perhaps the most common automatic emergency epinephrine injection device is commercially available from DEY, Inc. of Napa, Calif. under the trade designation EpiPen. The EpiPen device, believed to be described in U.S. Pat. No. 4,031,893, is designed to inject rapidly an adult dose of about 0.30 milligrams of epinephrine. The device is generally tubular and, including its tubular container, is about six inches long and nearly one inch in diameter. The device is relatively bulky and requires several manipulative steps in its use. Where a patient may only actually use the device infrequently, there may be some confusion in performing the required manipulative steps, particularly when the individual experiencing an anaphylactic reaction may be in a state of near panic. Although the device includes written instructions on its cylindrical surface, they may not be easily read, particularly under the stress of emergency circumstances. The manner in which the EpiPen is to be used is not readily and intuitively apparent without reading the text of the instructions on the cylindrical sleeve. Should it be necessary for someone other than the patient (e.g., a bystander) to administer the medication, for example, if the patient has gone into shock, the person called on to administer the medication may not know how to operate the auto-injection device. Consequently, precious time may be lost, increasing the risk to the patient. Additionally, after the device has been used to effect an injection, its hypodermic needle remains exposed, presenting post-injection hazards. Among such hazards are those associated with blood-born diseases such as HIV and hepatitis B and C or, when some of the medication remains in the device after injection, the risk of delivering some of the residual medication as a consequence of an accidental needle stick.

It would be desirable to provide a more compact, low profile, easily used auto-injector for rapid transcutaneous administration of a predetermined dose of medication.

SUMMARY

Our single-use, auto-injector for rapid delivery of a bolus of medication is configured to have a generally flat sealed housing with peripheral dimensions approximating those of a credit card to facilitate the ease and convenience of carrying, handling and using the device. The housing contains internal components configured and arranged to be in a generally flat array and to operate within the generally flat confines of the housing. The internal components include a syringe that is pre-filled with the selected injectable medication, the syringe including a syringe body and a hypodermic needle. The syringe is arranged to be moveable from a retracted, pre-injection position in which the device is stored, to an extended, injection position in which the needle extends out of the housing to penetrate tissue. The syringe itself is configured to be containable within a flat virtual envelope. A needle shield also may be carried by the housing to cover and enclose the hypodermic needle at all times before, during and after injection, so that the sharp tip of the needle is never exposed. The shield also may serve as an actuator, responsive to being pressed against the injection site to enable the needle to be driven from its retracted position to its injection position, first to pierce the patient's skin to the desired depth and then to inject automatically and rapidly a measured bolus of medication into the patient. When the device is actuated, the syringe is released from its retracted position to enable a self-contained power source first to drive the syringe toward the injection position and then to effect the injection of the medication. After injection, as the device is withdrawn from the patient, the needle shield automatically extends to a position to cover the needle. The device automatically locks the needle shield in its extended, needle-protective position. In another aspect, the generally flat configuration of the device provides ample space on which relatively large, easily understood, pictograms can be placed, graphically showing the manner of using the device or for providing other information.

The auto-injector includes a cover that is secured to the housing to contain and seal the injection end of the device, including the needle shield, during storage and before use. The cover is sealed to the housing and protects the device from inadvertent actuation. It must be removed in order to permit injection which is effected by then simply pressing the needle shield against the patient's skin. The cover may be transparent to enable the actuating member to be seen. The device may include a removable tamper-evident seal between the cover and the body of the device to further assure sterility and protection of the device before use.

It is among our general objects to provide a compact, portable, low-profile, safety, single use, auto-injector for rapidly administering a bolus of injectable medication and methods for rapid self-administration of medication. Other objects, advantages, aspects and features will be apparent to those skilled the art from the following, more detailed, description.

DESCRIPTION OF THE DRAWINGS

In the accompanying drawings:

FIG. 1 is an isometric view of an exemplary embodiment of an auto-injector, illustrating the back face of the housing and a large, flat labeling area;

FIG. 1A is an enlarged illustration of a peel-away strip connecting the cover to the body of the auto-injector;

DETAILED DESCRIPTION

Figure 1B:
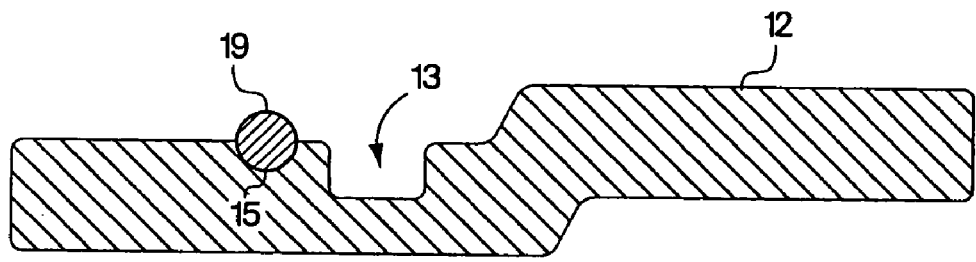
FIG. 1B is an enlarged cross-sectional illustration of the body of the injector illustrating the seal and groove on the auto-injector body adapted to receive and engage the cover.

FIGS. 1-6 illustrate a compact, low profile, auto-injector that includes a generally flat housing 10. The housing may be defined by a pair of mating, separately formed housing sections, including a front section 12 and a back section 14. The front and back housing sections 12, 14 may be formed from any appropriate material having sufficient strength to serve as a protective housing for the internal components of the device. The housing sections may be made from a thin injection molded metal or high pressure casting or from various polymers or engineered materials having sufficient structural and engineering characteristics, including rigidity and toughness, to insure the integrity of the internal components. The internal surfaces of the housing sections 12, 14 may be formed to include a number of walls and sockets that serve to cooperate with the internal components of the device to maintain the components in place as well as to guide movable components along their intended paths of movement.

The auto-injector may be considered as having a rear end 16 and a forward end 18 and a longitudinal axis extending between the ends. The device is intended to be held by its rearward portions, with the forward end 18 being pressed against the patient's skin, such as against the thigh. When triggered, the device causes the injection needle to emerge, suddenly, from the front end and effect injection of the medication bolus.

A molded safety cover 20 is fitted onto the forward end of the housing 10. The safety cover 20 maintains the sterility of the internal components and also prevents inadvertent actuation of the device. The safety cover 20 must be removed from the device before it can be used. The cover 20 preferably is formed from a moldable polymeric material having sufficient strength to protect the front end of the housing even under rough conditions. The material also should be selected to enable the formation of a thin, tearable connector by which a peel-away strip 11 may be attached to the body of the cover. The cover 20 may be transparent to enable the forward end of the housing including an actuator, described below, to be visible without removing the cap. The device is used in a simple three-step process, first by simply removing the peel-away strip 11, then gripping the rear end with one hand while removing the safety cover 20 with the other hand, and then pressing the exposed forward end of the device against the injection site. The outer surface of the housing 10 may be provided with over-molded elastomeric grips 28, 30 having frictional characteristics for holding the device securely in one hand. The elastomeric material of the grips 28, 30 may be provided with an appropriate filler to enable the device to glow in a dark environment.

Figure 1C:
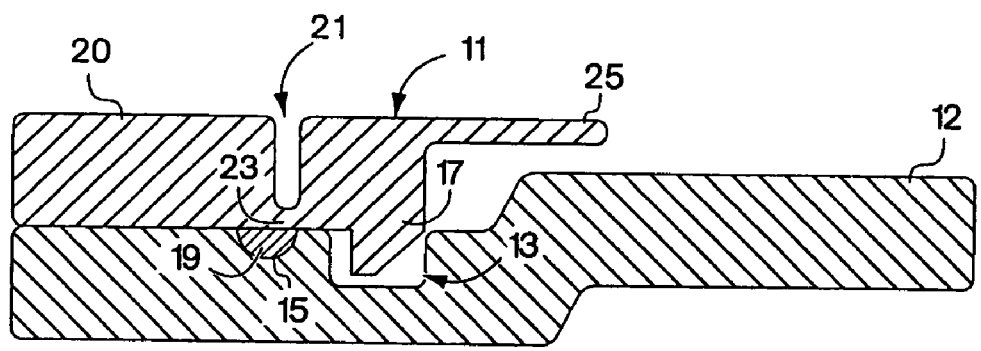
FIG. 1C is a cross-sectional illustration similar to FIG. 1B showing the cover engaged with the body, sealed and locked.
Figure 2:
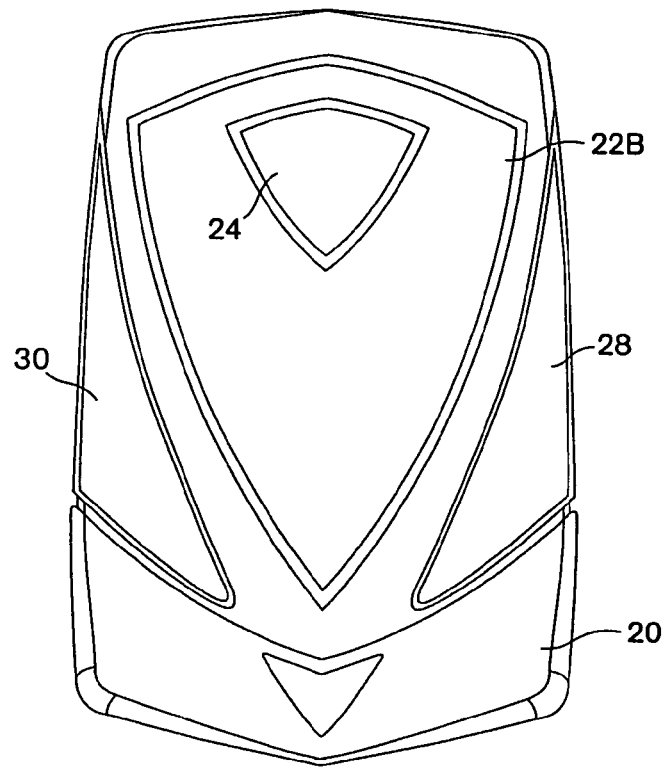
FIG. 2 is a plan view of the front of the device.

FIGS. 1A, 1B and 1C illustrate, in enlarged detail, the configuration of the housing 10 and the manner in which it interacts with the cover 20 and peel-away strip 11. Each of the front and back sections 12, 14 of the housing is formed with a first circumferential groove 13 and a second circumferential groove 15 located close to but forwardly of the first groove 13. The first groove 13 is intended to receive a latch portion 17 of the strip 11 (FIG. 1C). The second groove 15 is receptive to a compressible member, such as a molded gasket or O-ring 19. The peel-away strip 11 may be formed integrally with the cover 20, with the peel-away strip 11 being defined by a groove 21 formed circumferentially about the cover. The groove 21, in turn, defines a thin circumferential connector 23. The material of the cover 20 and peel-away strip 10 preferably is selected to be of a suitable polymer capable of protecting the forward end of the housing while also being tearable manually at the thin neck 23. A tab 25 preferably is integral with and extends from the peel-away strip 11 to facilitate gripping and tearing of the strip. The cover 20 is assembled with the housing simply by inserting the forward end of the housing 10 into the rearwardly facing opening of the cover. As the peel-away strip 11 advances rearwardly toward the first groove 13, it rides over the compressible gasket 19. The lower, rearward facing edge of the locking element 17 preferably is beveled, as at 27, to facilitate advancement of the peel-away strip 11 over and past the gasket 19. When the lock portion 17 of the peel-away strip 11 reaches the first groove, it snaps into the groove 13, preventing the cover from being removed until the strip 11 has been peeled away. When the device is in its stored configuration (FIG. 1C), the compressed gasket 19 provides a seal between the inner surface of the cover 20 and the outer surface of the housing 10 to provide a barrier against contamination.

Figure 3:
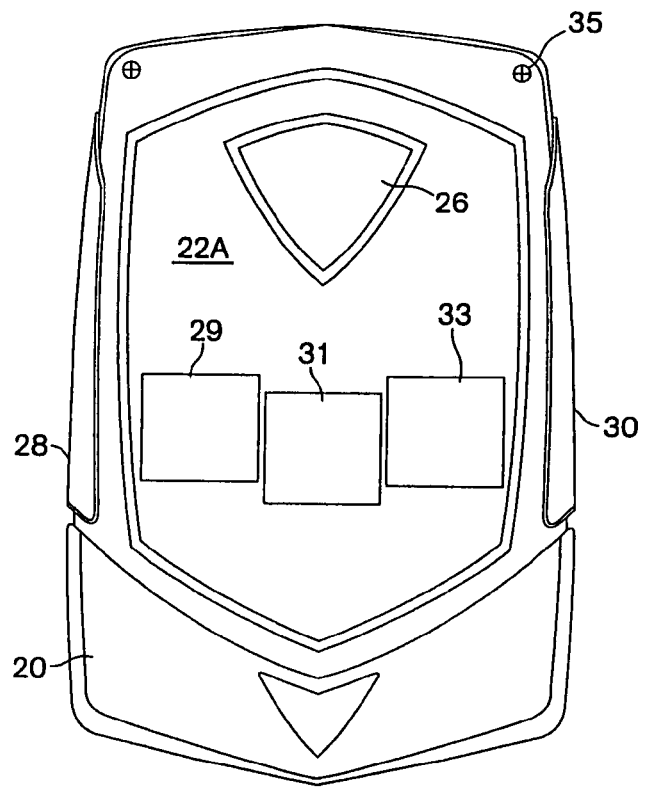
FIG. 3 is a plan view of the back of the device.
Figure 4:
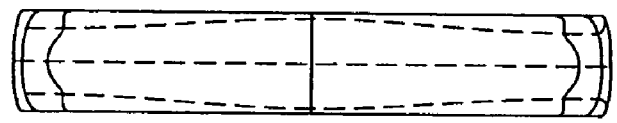
FIG. 4 is an end view of the rear of the device.
Figure 5:
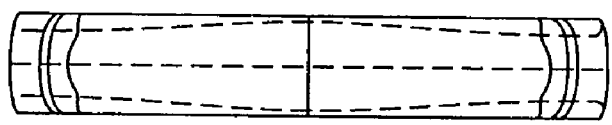
FIG. 5 is an end view of the front of the device with the cover attached to the housing.
Figure 6:
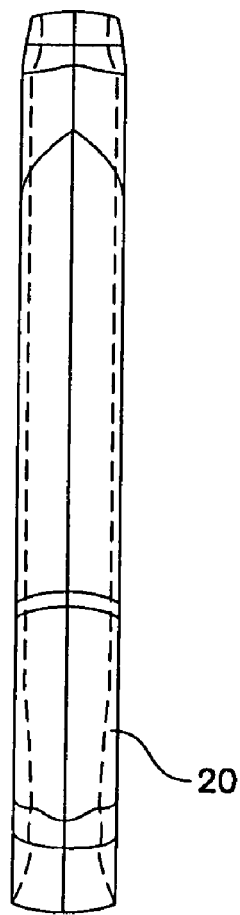
FIG. 6 is a side elevation of the device.

The flat configuration of the housing enables each of the front and back housing sections 12, 14 to receive a label. The labeling area of at least one of the sections, e.g., the back section 14, is of sufficient size to receive graphic images such as pictograms illustrating use of the device. As shown in FIG. 3, the label 22A has three pictograms, 29, 31, 33 illustrating, respectively, removal of the peel-away strip 11, removal of the cover and pressing the forward end against the injection site. The use of such graphics enables even one unfamiliar with the device to understand immediately how it is used.

Figure 7:
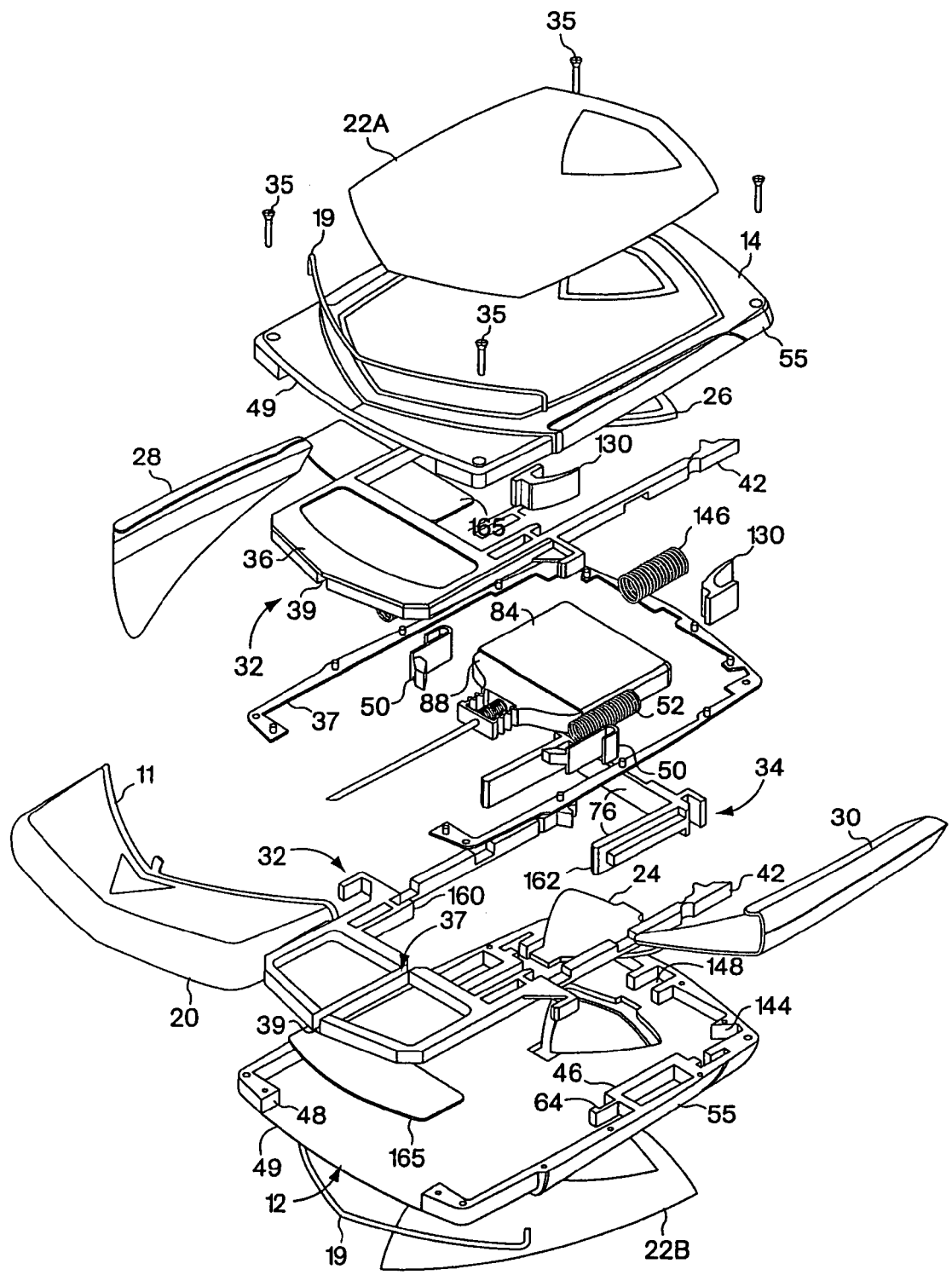
FIG. 7 is an exploded illustration of the components of an exemplary embodiment of the device.

The front and back sections 12, 14 of the housing 10 may be secured together in a manner compatible with the particular materials from which the housing is made. For example, if the housing is made from an injection molded or cast metal, the sections may be secured together with screws 35 (FIG. 7) or an appropriate adhesive. The peripheral portions of the front and back sections 12, 14, may be sealed by interposing a thin gasket 37 between the facing surfaces of the peripheral walls of the housing sections. The gasket or O-ring 19 should maintain a seal where it contacts the thin gasket 37. Should the front and back housing sections be formed from a plastic or engineered material, the sections 12, 14 may be sealed by sonic welding, adhesives or other bonding agents, as appropriate.

Each of the front and back housing sections 12, 14 may be provided with a window 24, 26, respectively, through which the condition of the medication in the syringe can be observed. For example, in the case of epinephrine, the presence of dark brown color or a precipitate in the medicine indicates that the strength of the medication has become reduced or that it has lost its therapeutic function, signaling that the medicine is not reliable and that the device should be replaced. The window should be formed from a material, or should be coated, to prevent exposure of the medication to quantities of ultraviolet light that might adversely effect its medicinal characteristics. When the device is used with medications for which visual inspection is not particularly critical, the window may be modified or omitted. Omission of the window provides for additional flat surface on which labels may be placed appropriate to the particular medication or intended use of the device.

The device preferably is dimensioned to be held in one's palm and may have peripheral dimensions approximating those of a conventional credit card. In a preferred illustrative example, the housing may be about 3.25 inches long, and about 2.0 inches wide. The thickness of the device is substantially less than either of the length or width and, in the preferred illustrative example, may be of the order of 0.25 inch thick. The device, so dimensioned, has a generally flat appearance. It is carried easily in ones pocket or purse without feeling bulky or uncomfortable thereby increasing the likelihood of it being carried on one's person and being available, if needed. It should be understood, however, the foregoing dimensions are illustrative only and that the precise dimensions and peripheral shape of the device may be varied as long as the device maintains its compact configuration and is not made so large as to defeat its compact and portable characteristics.

The term "flat" when used in this specification to describe the housing of the device is intended to mean a configuration that can be confined in a virtual three dimensional envelope having a length, a width, and a thickness, and in which the thickness is substantially less than each of the length and width, with each of the length, width and thickness being measured along orthogonal directions. Although the embodiments described in this specification may be considered as having a generally rectangular peripheral configuration, other, non-rectangularly configured housings may be employed that have orthogonally measured length, width and thickness of a flat virtual envelope, as defined. It also should be understood that "flat" is not intended to be limited to precisely planar in a mathematical sense.

Although the most preferred embodiment has peripheral dimensions approximating those of a credit card (2.125"×3.375") and a thickness of about 0.25 inch, the dimensions of the device may be varied while still maintaining the flat characteristic described in the specification. Preferably, a range of lengths between about 2.8 to about 3.8 inches may be employed with a width in the range of about 1.7 to about 3.5 inches. The thickness of the device may be between about 0.20 to about 0.75 inch.

Figure 8:
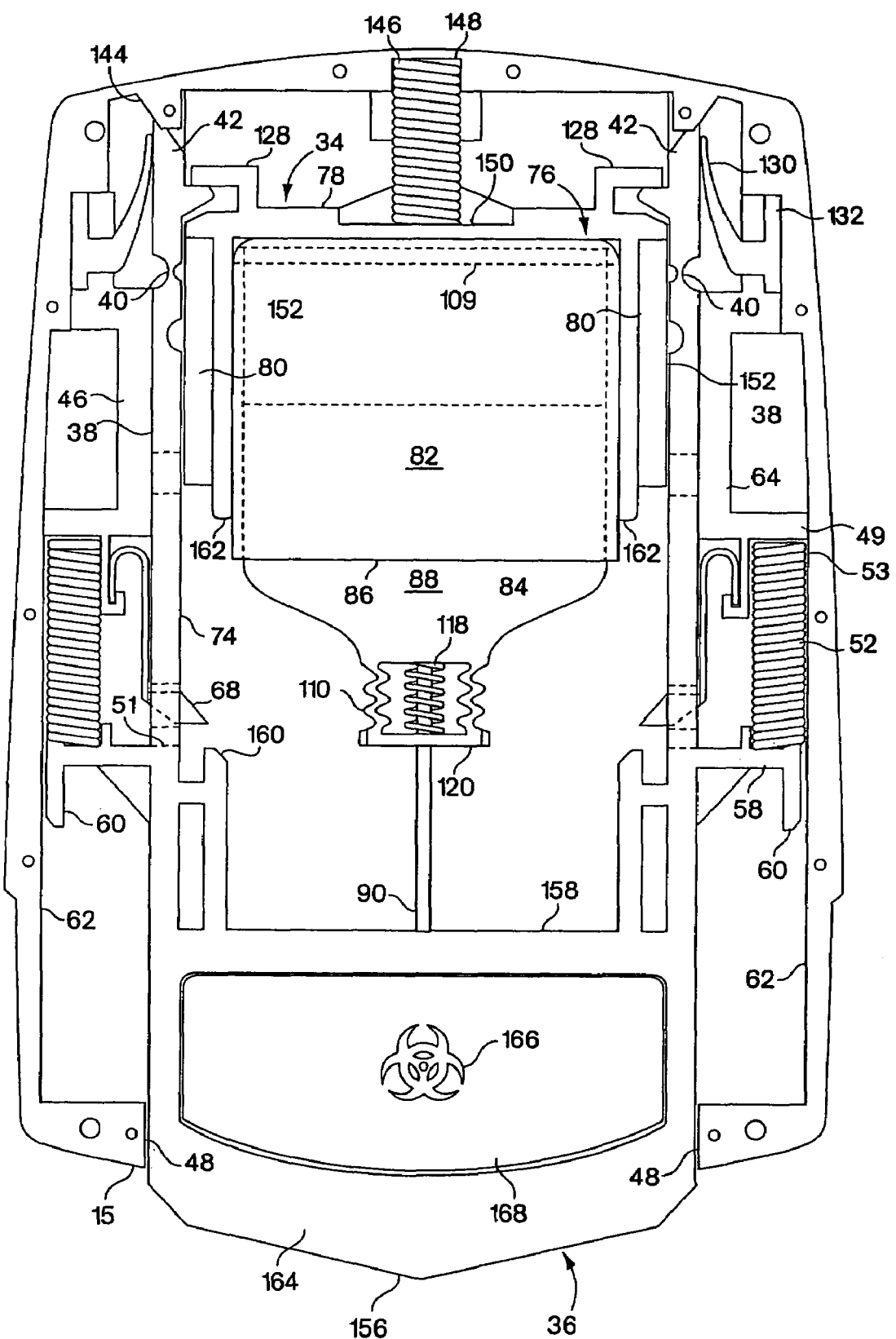
FIG. 8 is a plan view of the internal components of the device with one section of the housing removed, illustrating the components in a retracted configuration, in readiness for use.
Figure 9:
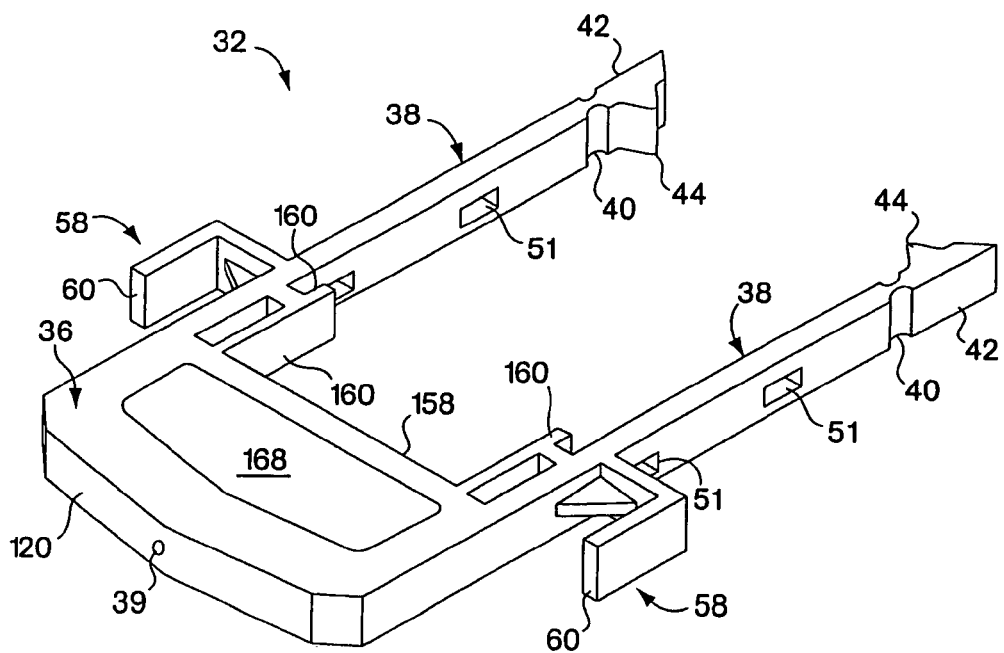
FIG. 9 is an isometrical illustration of the actuator assembly.
Figure 10:
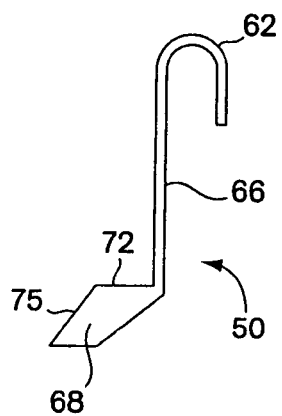
FIG. 10 is an enlarged illustration of one of the arm locks.

FIGS. 7-15 illustrate the internal components of an exemplary device embodying aspects of the invention. The device may be considered to include two longitudinally sliding assemblies, including an actuator assembly 32 and a syringe carrier assembly 34. The actuator assembly 32 (FIG. 9), which may be formed from molded plastic mirror-image mating sections (see FIG. 8) in the same manner as the mating housing sections 12, 14, includes a generally flat needle shield 36 at its forward end and a trailing portion, such as a pair of arms 38 extending rearwardly from the shield 36. The needle shield 36 has an internal needle passage 37 adapted to contain the forward end of the needle. The passage terminates, at its forward end at an opening 39. The trailing end of each arm 38 includes a living hinge 40 by which a finger 42 is flexibly attached to the arm 38. Each finger 42 includes a radially inwardly extending detent 44 that cooperates with the syringe carrier assembly 34 in a manner described below. The laterally outward surfaces of the arms 38 are slidably guided by a pair of guide walls 46, formed integrally with the front and back housing sections 12, 14, and guide surfaces 48 formed at the forward end of the housing 10. The guide surfaces 48 define a forward opening 49 in the housing through which a forward portion of the needle shield 36 projects. The actuator assembly 32 is retained in the retracted position shown in FIG. 8 by a pair of releasable arm locks 50 that are mounted interiorly of the housing and releasably engage forward apertures 51 formed in the arms 38 of the actuator assembly 32 (FIGS. 8 and 9). When the actuator assembly 32 is in its retracted position (FIG. 8), the forward portion of the needle shield 36 projects slightly beyond the forward end 15 of the housing 10. When the cover 20 is separated from the housing, the forward end of the needle shield 36 is exposed and serves as an actuator to initiate operation of the device, when pressed against the patient's skin. The actuator 32, or at least the portion of the needle shield 36 that projects forwardly of the housing before the device is actuated, may be formed from or provided with a label that has a visually distinct appearance from that of the housing, for example, by providing it with a red color or other warning indicia. When the cover 20 is transparent, the distinct forward portion of the shield is visible through the cover enhancing an understanding of the operation of the device merely from its appearance.

The actuator assembly 32 is biased in a forward direction by a pair of longitudinally disposed side compression springs 52. One end of each side spring 52 is captured in a socket 54 defined by walls 49, 53 and the sidewalls 55 of the housing molded as part of the housing sections 12, 14. The other, forward, end of each side spring 52 is captured in a socket 56 (FIG. 11) defined by each of a pair of outriggers 58 that extends laterally from its associated arm 38. The outermost end of each outrigger 58 terminates in a guide member 60 that slides along and is guided by a longitudinally extending surface 62 of the sidewall formed by the mated housing sections 12, 14. When the device is in the storage configuration shown in FIG. 8, the side springs 52 are substantially, but not completely, compressed. The springs 52 can be compressed further in order to permit the entire actuator assembly 32 to move slightly proximally to trigger the injection procedure, as described below.

The actuator assembly 32 is releasably maintained in the retracted configuration shown in FIG. 8 by the releasable arm locks 50. As shown in enlarged detail in FIG. 10 each arm lock 50 has a retained end 62 that may be U-shaped and is captured in a socket 64 formed by cooperative walls of each of the front and back housing sections 12, 14. The arm locks 50 may be formed from a suitable plastic having characteristics that will enable it to perform its spring function. Each arm lock 50 includes an extension 66 that functions in the manner of a resilient leaf spring. The end of each extension 66 has an inwardly projecting finger 68 that extends laterally inwardly through a distal aperture 51 formed in its associated arm 38 of the actuator assembly 32. The extension 66 includes a flat section 72 that engages squarely a surface 70 (FIG. 11) that defines the aperture 51 in the arm 38. The tip of the finger 68 extends inwardly beyond the inner surface 74 of the arm and defines an inclined, wedge surface 75 that, when engaged, trips the locks 50 and as described below, releases the arms 38, permitting the entire actuator assembly 32 to be driven distally under the influence of the side springs 52. The arm locks 50 are tripped automatically when the injection needle has penetrated the patient's skin to the desired depth and the injection has been made.

The syringe carrier assembly 34 includes a syringe carrier 76 and a syringe 82, pre-filled with a selected injectable medication. For the syringes described, the syringe carrier 76 may be U-shaped, defined by an upper wall 78 and a pair of downwardly extending sidewalls 80. In this exemplary embodiment, the syringe 82 has a flat configuration and is defined by a flat plunger-type device comprising a cup-like container 84 having an open end 86 that receives a plunger 88 that carries an injection needle 90. The syringe carrier 76 is connected securely to the syringe, for example, by dimensioning the container 84 and carrier 76 to provide a snug friction fit which may be supplemented by lugs 85 extending from the carrier sidewalls 80 that engage the forward edge of the container.

Figure 16:
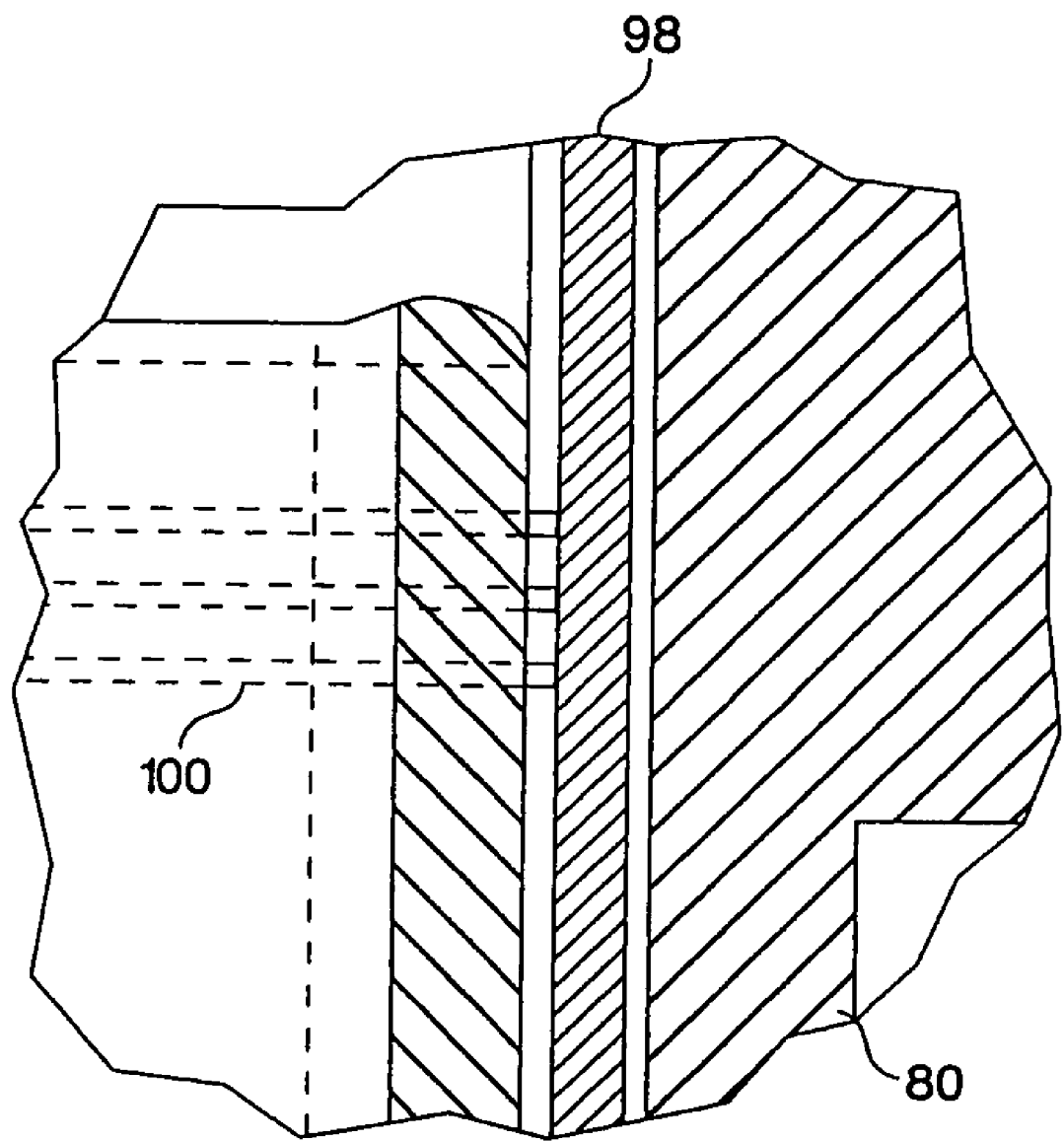
FIG. 16 is a sectional illustration of a portion of the plunger and container of the syringe body of FIG. 14 illustrating the seal between the two.
Figure 17:
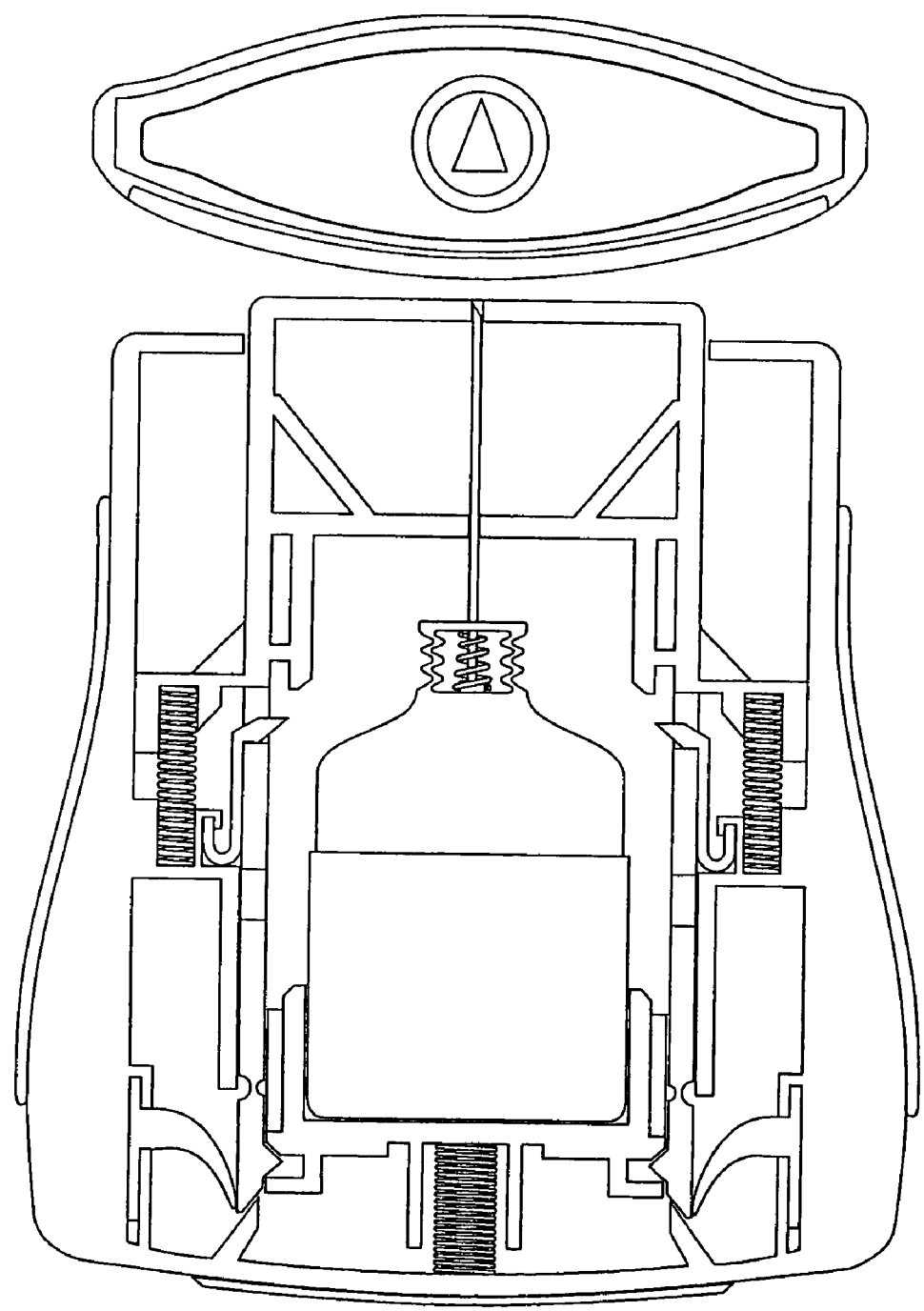
FIGS. 17-22 are sequential illustrations of the device in various stages of operation.

In a device in which the medication to be contained in the container 84 may be epinephrine, the container 84 preferably is formed from glass and is transparent so that its front and back faces 92, 94 (FIG. 15) may serve as windows. The windows are located to be aligned with the windows 24, 26 on the front and back housing sections 12, 14, when the device is in its retracted configuration (FIG. 8). In that manner, the user may observe the contained liquid through the windows to determine visually its condition. This is particularly important with a medication which changes color or forms a precipitate when its medicinal effectiveness has been reduced or lost. It should be understood that, although use of a glass container 84 is desirable when the medication is epinephrine, the container 84 may be formed from a variety of other materials that are compatible with the particular medication to be contained. In this embodiment, the container 84 has a flat configuration in which the thickness T of the container is substantially less than either of its length L or width W (see FIGS. 14, 15). The container 84 has front and back walls 92, 94 joined by a peripheral wall 96 that is securely engageable by the syringe carrier 76. The open end 86 of the container faces forwardly and is closed by the flat plunger 88 that is slidable into the container 84. The plunger 88 engages the internal surfaces of the front and back walls 92, 94 as well as the side portions 98 of the peripheral wall 96. The outer surface of the plunger should be slidably sealed to the container as by providing the plunger with one, and preferably several, wiping ribs 100 that extend about the plunger 88 to engage with the internal surfaces of the walls 92, 94, 96 (FIG. 16). The peripheral wall may be radiused, if desired, to facilitate an enhanced seal between the container 84 and plunger 88. The plunger itself may be solid or hollow, depending on the volume of medication to be contained and should be formed from a material that is compatible with the contained medicine, such as rubber or other compositions of the type used in conventional tubular syringes. The hollow plunger illustrated in FIGS. 14 and 15 may be considered as having front and back walls 102, 104 and a peripheral wall 106 The rear end 108 of the plunger 88 is open to communicate with the interior of the container 84.

Figure 13:
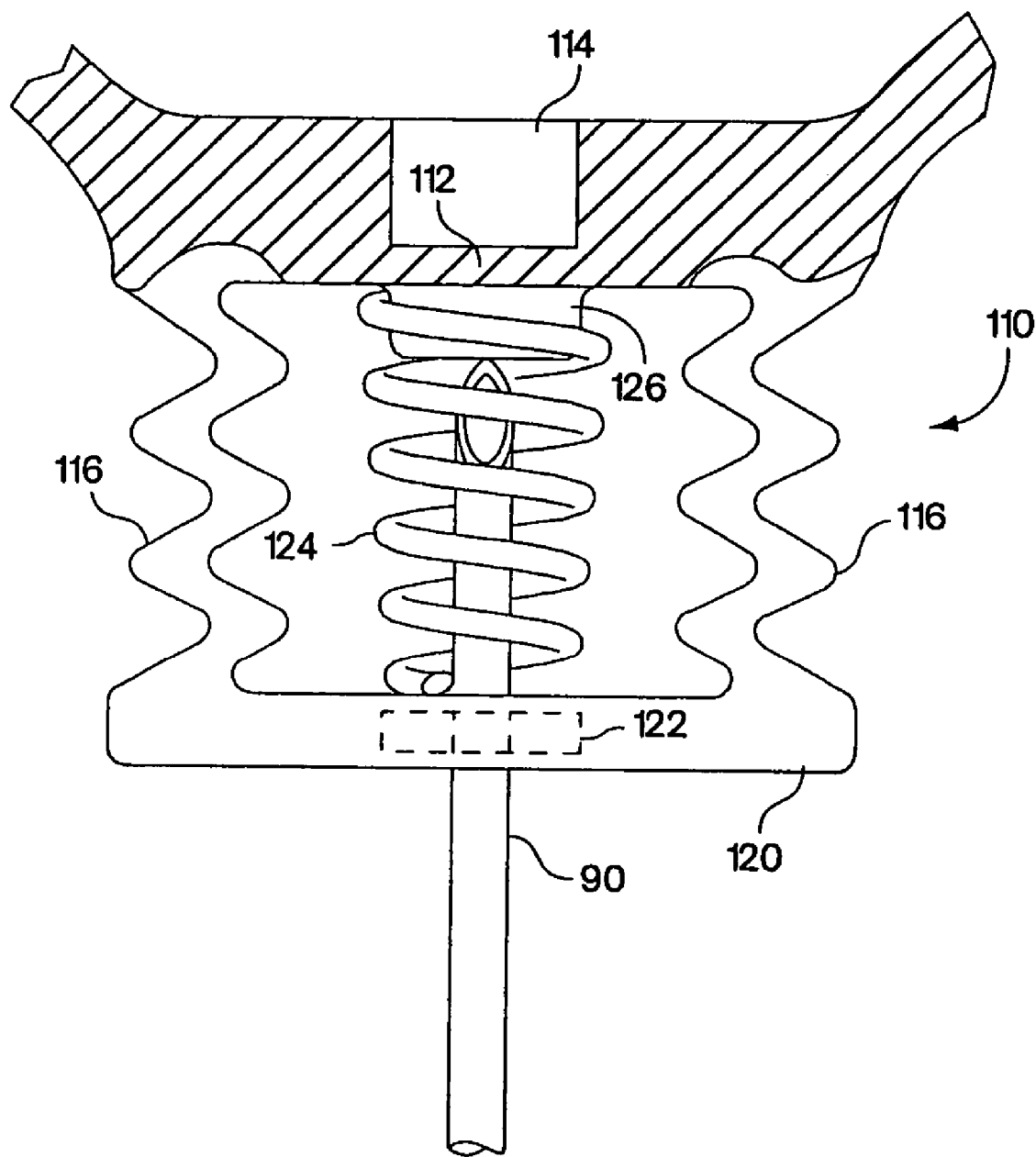
FIG. 13 is an enlarged illustration, partly in sections, of the arrangement for supporting a hypodermic needle.
Figure 14:
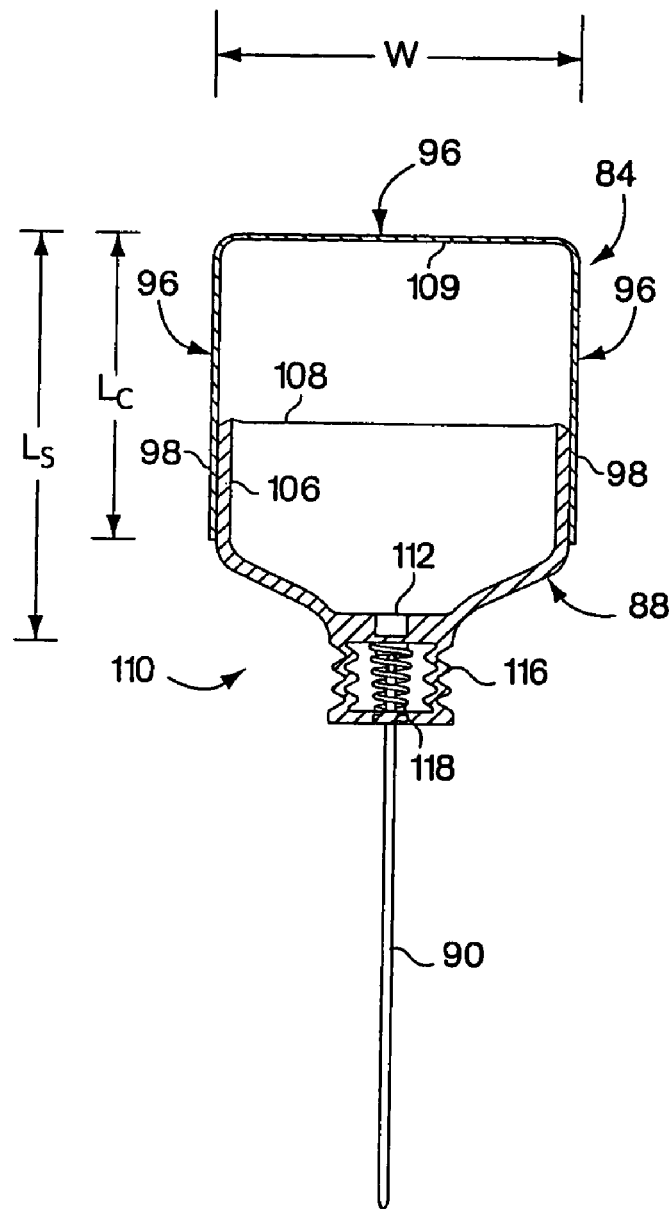
FIG. 14 is a front view of an embodiment of a syringe.
Figure 15:
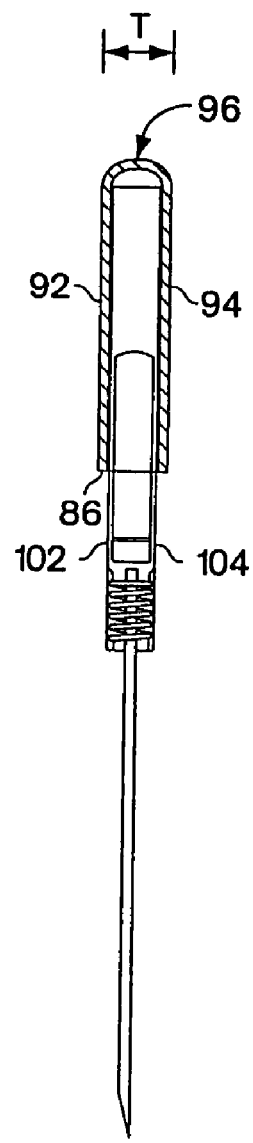
FIG. 15 is a side view of the syringe of FIG. 14.

In this embodiment, the forward end of the plunger 88 includes a needle carrier 110 by which the injection needle 90 is held in spaced alignment with a septum 112 that forms a seal at the forward end of the plunger (FIG. 13). The septum 112 completely closes the forward end of a passage 114 that extends through the wall of the plunger and communicates with the interior volume of the syringe. The needle carrier 110 may include a pair of longitudinally collapsible, forwardly extending, accordion-like supports 116 that may be biased in a distally extended configuration, by a compression spring 118. The double-ended needle 90 may be secured to an anchor 122 that can be embedded, together with a portion of the needle, in the needle support 120. The sharp rear tip of the needle should be non-coring, and is supported in slightly spaced relation to the forward side of the septum 112. The sharp rear end of the needle 90 is maintained in spaced relation to the outer surface of the septum 112 by the compression spring 118 that extends between the septum 112 and the needle support 120. When the needle is in flow communication with the syringe body, the flow passage from the syringe body, into and through the needle should be unobstructed and sufficient to enable rapid delivery of the bolus of the medication. The rear end of the compression spring 124 may be retained in place by a boss 126 formed about the forward face of the septum 112 and adapted to engage the rear end of the compression spring 124. The forward end of the spring 124 is tapered and bears against the needle support, with the spring surrounding the forward end of the needle 90.

In this description and in the claims of this specification, the term "syringe" is intended to mean a syringe body adapted to contain injectable medicine in which the body has an interior collapsible volume with a hypodermic needle carried by the syringe body and being connected or connectible to the interior chamber to enable mediation to be injected from the container through the needle into the patient. The above definition of "flat" when used to describe the syringe 82 is intended to have the same meaning as that discussed above in connection with the configuration of the housing, namely, as referring to a syringe body containable within a virtual envelope having a length, a width, and a thickness and in which the thickness is substantially less than each of the length and width, with each of the length, width and thickness being measured along directions orthogonally related to the others. Thus, the described arrangement of the syringe 82 may be considered to comprise a flat syringe. Although two specific configurations of flat syringes are described in this specification, it should be understood that other syringe configurations, containable in the flat housing, may be employed in the practice of the invention.

Figure 11:
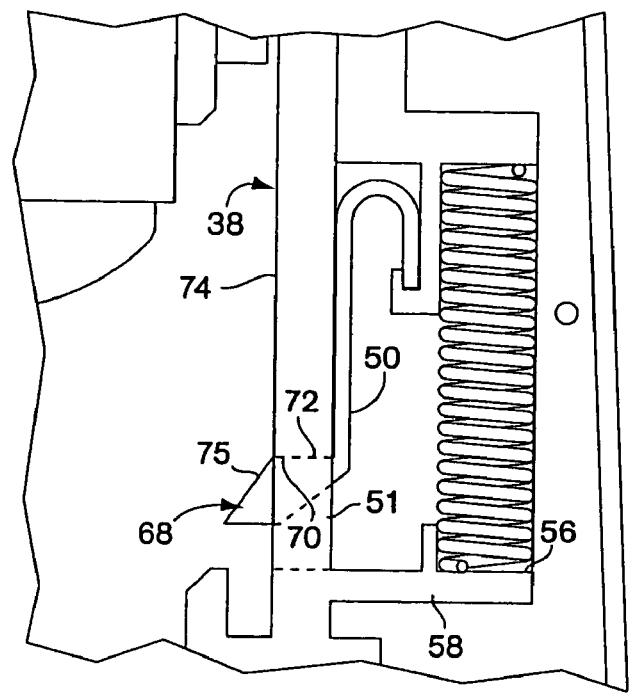
FIG. 11 is an enlarged plan illustration of one of the arm locks and its engagement with an arm of the actuator assembly and a spring for biasing the actuator assembly in a forward direction.
Figure 12:
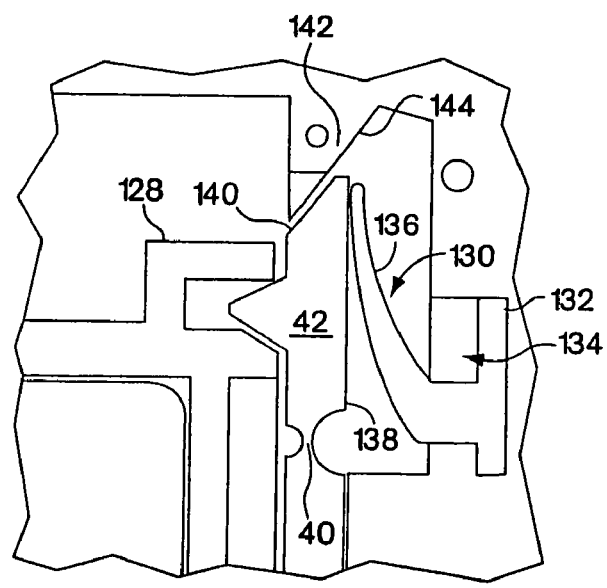
FIG. 12 is an enlarged illustration of one of the latching arrangements for retaining the syringe assembly in a retracted configuration, in readiness to be released.

As shown in FIGS. 8, 11 and 12, the syringe assembly 34 is restrained in its retracted position by engagement of a pair of latches 128 formed as part of the syringe carrier 76. Each of the latches 128 extends in a laterally outward direction and engages the detent 44 of one of the fingers 42 of the actuator assembly. Each of the fingers 42 is biased into locked engagement with the latch 128 by a latch spring 130. The latch spring 130 may include a base portion 132 which is secured in a socket 134 molded into the housing sections 12, 14, and a resilient member 136 that extends from the base 132 into engagement with the outwardly facing surface 138 of the finger 42. The free end 140 of each finger 42 may be beveled, as indicated at 140. The beveled free end 140 is biased into engagement with a wall 142 that includes a camming surface 144. The camming surface 144 is oriented with respect to its associated finger 42 to guide the finger 42 to pivot outwardly (clockwise as seen in FIG. 12) about the hinge 40 as the actuator assembly 32, including the finger 42, is moved slightly to a more retracted, proximal position. Such movement, initiated by pressing the forward end of the actuator against the injection site causes the fingers 42 to pivot outwardly, disengaging each detent 44 from its associated latch 128, and freeing the syringe assembly 34 for forward movement. The syringe assembly is biased for such movement by an injector compression spring 146. The injector spring 146 is retained, at its rear end, in a socket 148 formed integrally with the housing sections 12, 14. The forward end of the spring 146 bears against the upper wall 78 of the syringe assembly 34 where it is held by providing the upper wall with a retention boss or socket 150 engageable with the spring 112 (FIG. 8). The injector spring for some applications, especially those of an emergency nature, should develop enough force to drive the needle through clothing, in addition to tissue.

The injector spring 146 is configured so that with the actuator and syringe assemblies 32, 34 in the locked configuration (FIG. 8), the injector spring 112 is capable of a small amount of further longitudinal compression. The extent of additional longitudinal compression should enable the actuator and syringe assemblies 32, 34 to be retracted sufficiently to withdraw the detents 44 from locked engagement with the latches 128. When the latches 128 have been released, the syringe assembly 34 is released and is driven immediately and forcefully in a forward direction by the injector spring 146. The syringe assembly 34 is guided in that movement by engagement of the outer surfaces 152 of its sidewalls 80 with the inner surfaces 74 of the arms 38 of the actuator assembly 32.

As the syringe assembly 34 is driven forwardly, the sharp, forward tip of the injection needle 90 projects longitudinally through an aperture 154 in the needle shield 36 and beyond the forward end 156 of the needle shield 36. At this stage in the operation of the device, the forward end 156 remains pressed firmly against the user's skin and the force of the injector spring 146 will drive the needle 90 into the patient's tissue to an intended depth. The selected depth of needle penetration will depend, in part, on the type of medication to be injected and whether it is to be an intramuscular or subcutaneous injection. The depth of needle penetration is determined by the length of the needle and the needle shield as well as location of the needle when its forward advancement is terminated. In this embodiment forward movement of the needle terminates when the needle support 120 engages the rear face 158 of the needle shield 36. Throughout the advancement of the syringe assembly 34, the actuator assembly 32 remains locked in place by engagement of the arm locks 50 with the forward sockets 51 in the arms 38 of the actuator assembly 32.

When the needle 90 has penetrated the tissue to the intended depth, the needle support 120 will have bottomed on the rear face 158 of the needle shield 36 and the needle carrier 110 will begin to collapse, advancing the syringe body, including the septum 112, toward the rear end of the needle. Continued advancement causes the septum 112 to impale itself on the needle 90, establishing flow communication between the needle and the interior of the syringe. When the supports 116 have collapsed, the plunger 88 can no longer advance forwardly. The container 84, however, is free to continue forward advancement sliding over the plunger, under the continued force of the spring 146 and, in so doing, the internal volume of the syringe is compressed, causing ejection of a bolus of medication through the needle into the patient.

Different medications, of course, will require different doses. Additionally, depending on the nature of the medication, it may be desirable for the syringe to contain a greater volume of medication than the actual volume of the dose to be injected. For example, when the medication is epinephrine, (1:1000) an adult dose is considered to be 0.3 ml. The stability of the epinephrine, however, is improved when it is stored in a larger volume of about 2.0 ml. Therefore, the extent to which the internal volume of the syringe can compress may be limited to assure injection only of the desired dose. The volume of the injected dose may be limited by limiting the extent to which the internal volume of the syringe can be compressed. This can be accomplished, for example, by providing an abutment surface 160 internally of the housing. The abutment surface 160 is located to be in alignment with a forwardly facing surface 162 at the end of each of the container carrier sidewalls 80. When the ends 162 of the sidewalls 80 have engaged the abutment surfaces 160, forward movement of the container 84 is terminated, thus terminating the ejection stroke. Another approach to limiting the extent to which the syringe volume can be compressed is to dimension the container 84 and plunger 88 so that the rearward face 108 of the plunger bottoms out on the inner face of the rear portion 109 of the peripheral wall of the container 84.

Throughout the release of the syringe assembly 34 from its locked, restrained position until the time that the bolus of medication has been injected into the patient, the entire device is pressed firmly against the injection site. Throughout the time that the needle begins to protrude from the forward end 156 of the shield 36 until the time that the device is fully withdrawn from the injection site, no portion of the needle is visible or exposed.

As the syringe assembly 34 is driven forwardly by the injector spring 146, the actuator assembly 32 is restrained from moving forward relative to the housing 10 by engagement of the arm locks 50 with the arms 38. Engagement of the arm locks 50 with the arms 38 also serves to limit the extent of rearward travel of the actuator assembly during the initial triggering operation, as the forward surface 156 of the shield 36 is pressed against the injection site. As the syringe carrier 76 and syringe 82 approach the end of the injection stroke, the protruding ends 68 of the arm locks 50 are engaged by a portion of the container assembly, such as a portion of the lower ends 160 of the sidewalls 80 of the container carrier 76, thereby tripping the arm locks 50 to disengage from the arms 38 and permit the actuator assembly 32 to be driven forwardly with respect to the housing 10 under the influence of the side springs 52. This assures that the forward end 156 of the needle shield 36 will be continually and automatically pressed against the patient's skin as the device is withdrawn from the patient. Consequently, after the injection has been completed, withdrawal of the device from the patient enables the side springs 52 to simultaneously and progressively cause extension of the needle shield 36 to cover and completely contain the needle 90. The actuator assembly 32 and its needle shield 36 are permitted to move forwardly sufficiently to assure that when the device has been withdrawn to the point that it no longer contacts the skin, the needle is completely covered by the shield 36.

The outwardly facing surfaces 164 of the needle shield 36 that project beyond the forward end 15 of the housing 10 after the device has been used also provide a wide, flat area receptive to labeling 165 (FIG. 7) or other imprint with sharps biohazard warning symbols 166 (FIG. 8). The biohazard warning symbol 166 preferably is placed on the portion 168 of the more rearward surface of the needle shield that is exposed only when the shield has been extended to its post-injection, needle covering position. In order to assure that the needle shield cannot be inadvertently depressed to expose the needle after the device has been used, another detent aperture 170 is formed in each of the arms 36 rearward of the apertures 51, to receive and engage the latch 50 when the actuator assembly 32 and needle shield 36 have been projected to fully cover the needle 90. Thus, once the needle shield 36 has been extended to cover the needle, it is automatically locked in that protective configuration and no further steps are required in order to prevent accidental post-use needle stick.

Figure 18:
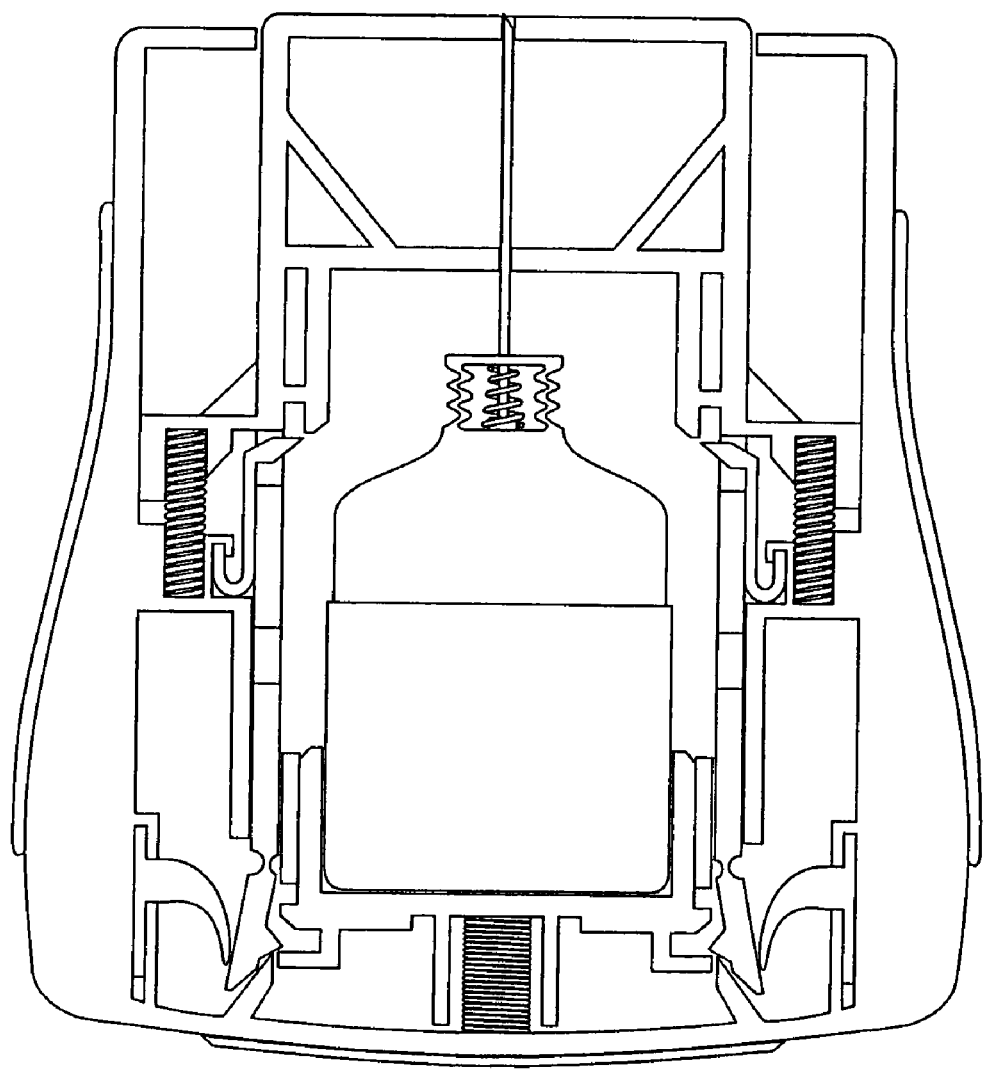
Figure 19:
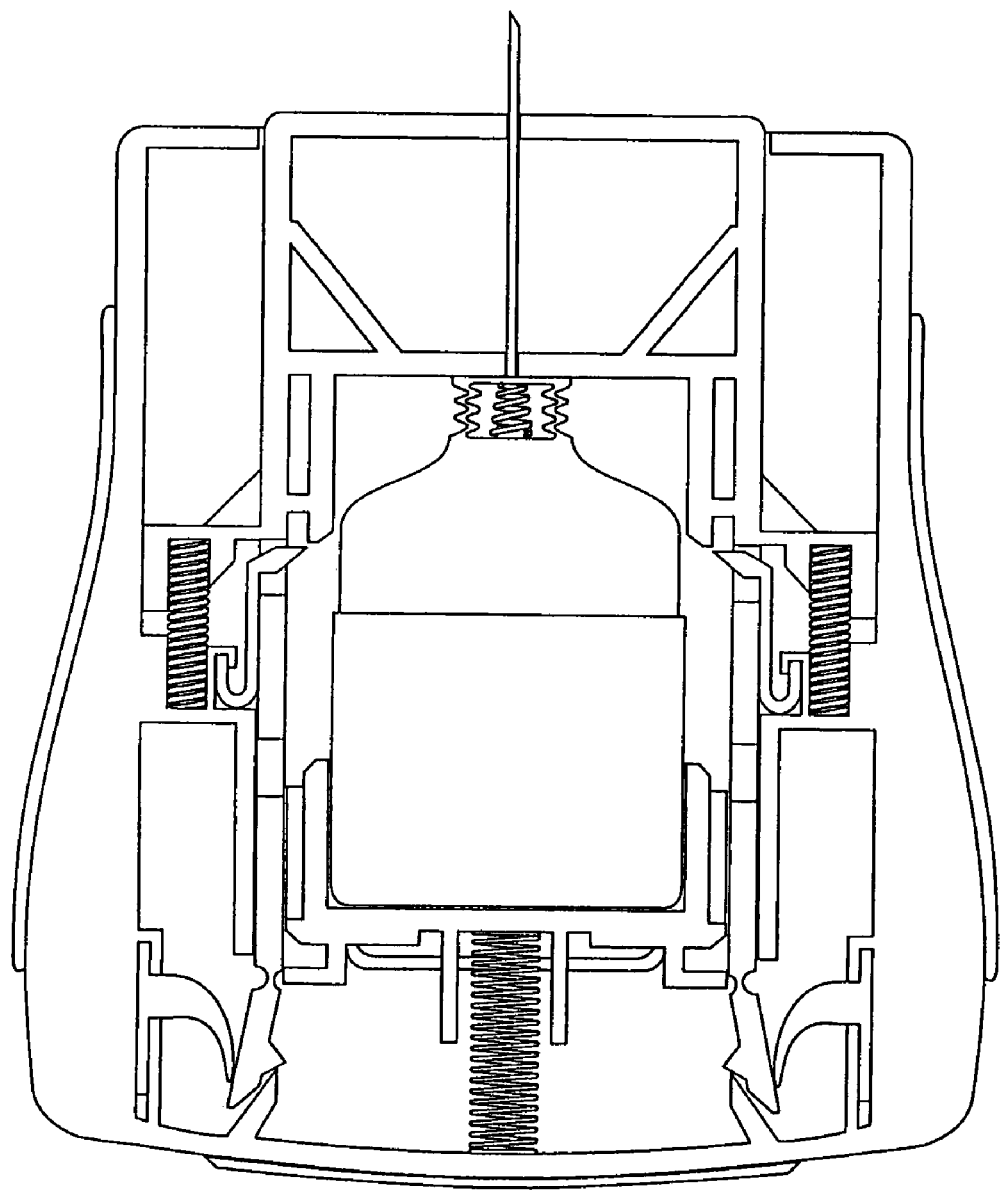
Figure 20:
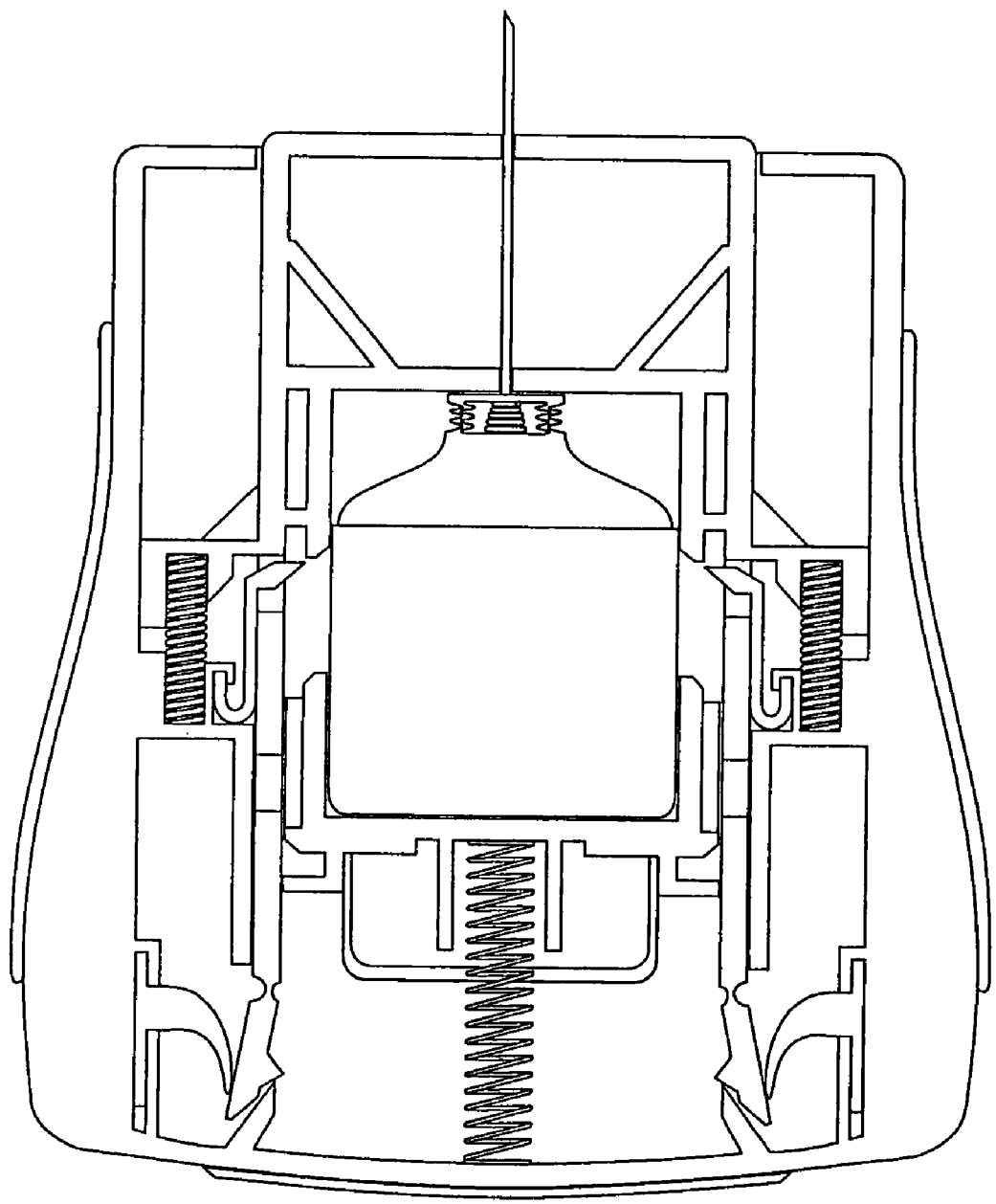
Figure 21:
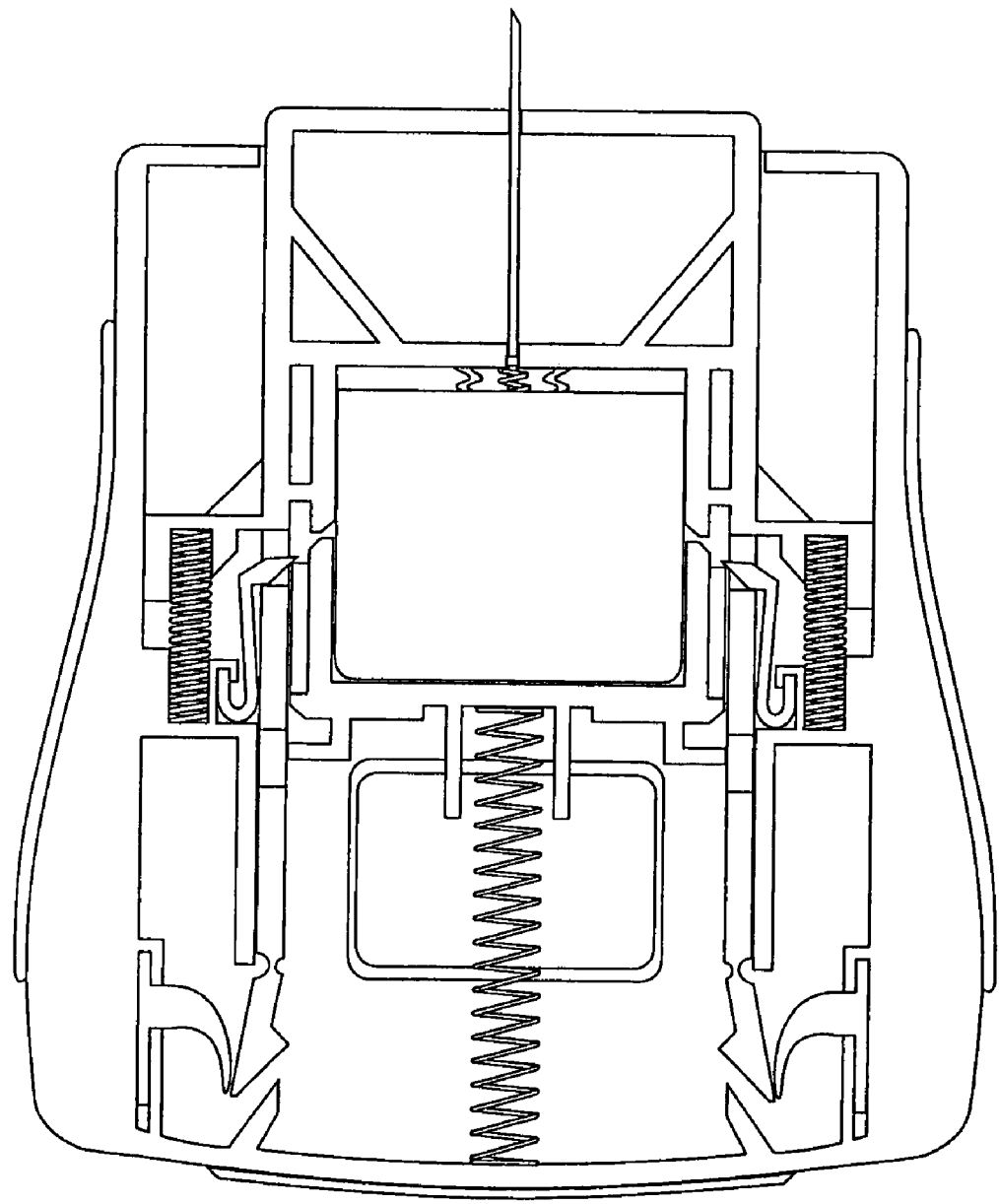
Figure 22:
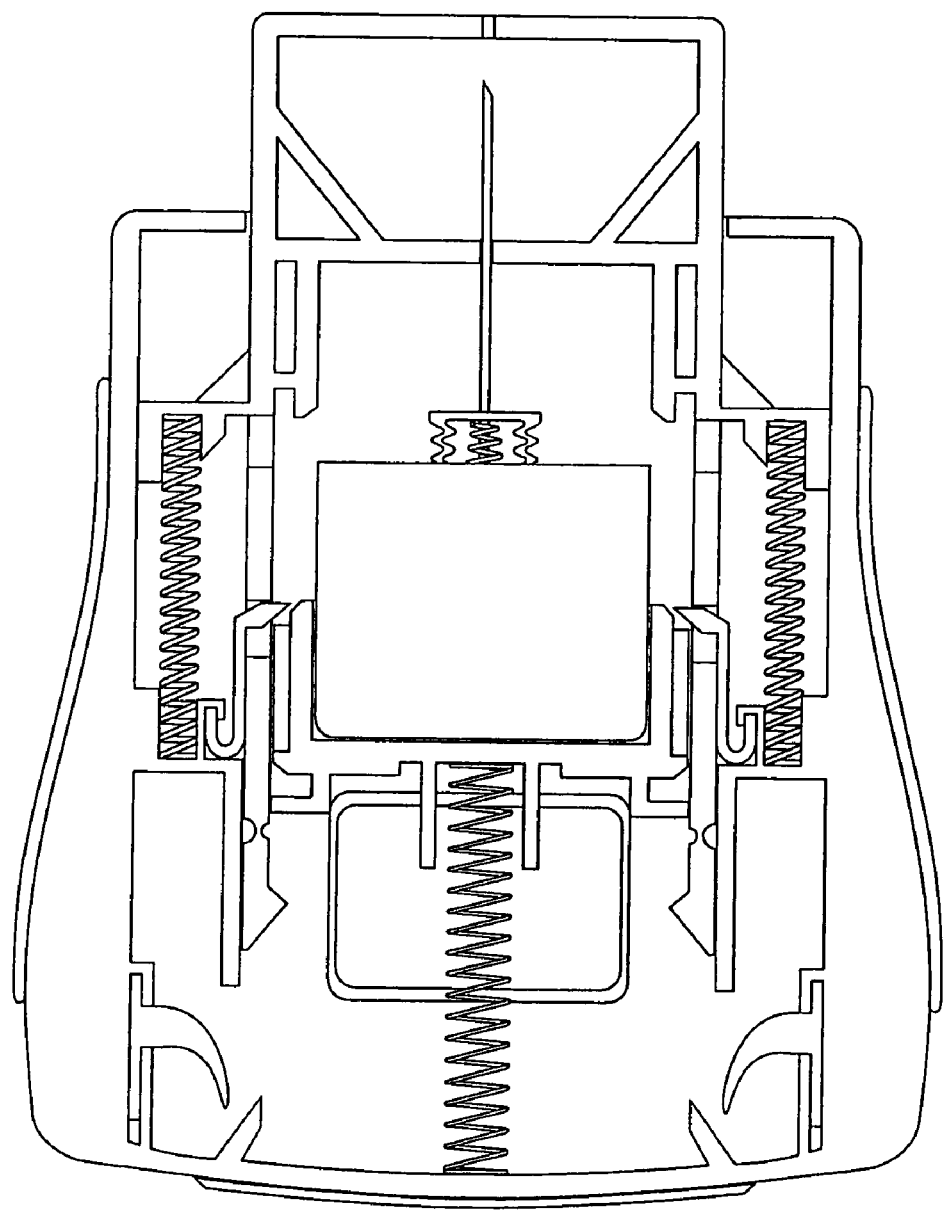
Figure 23:
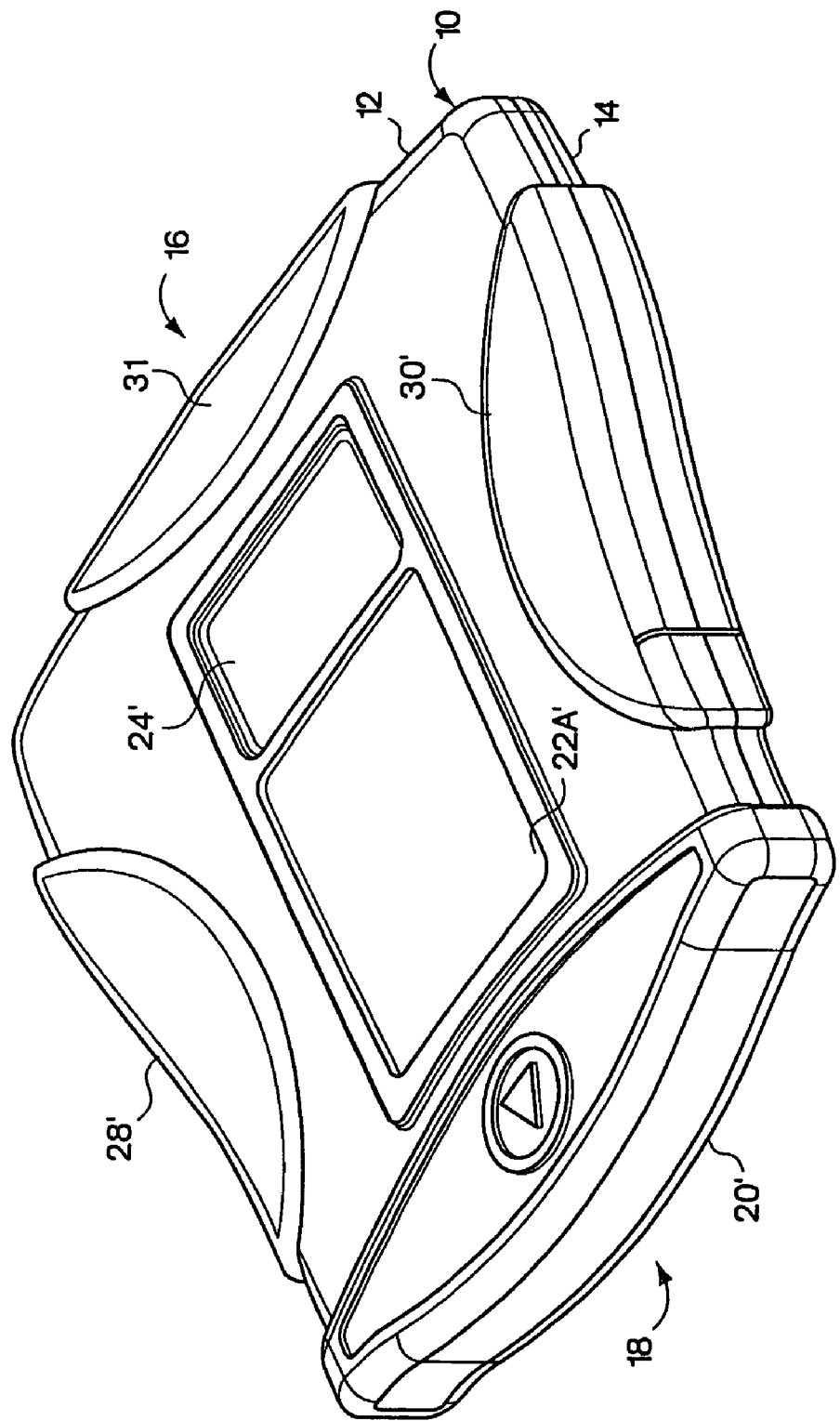
FIG. 23 is an illustration of another exemplary embodiment of a device.
Figure 24:
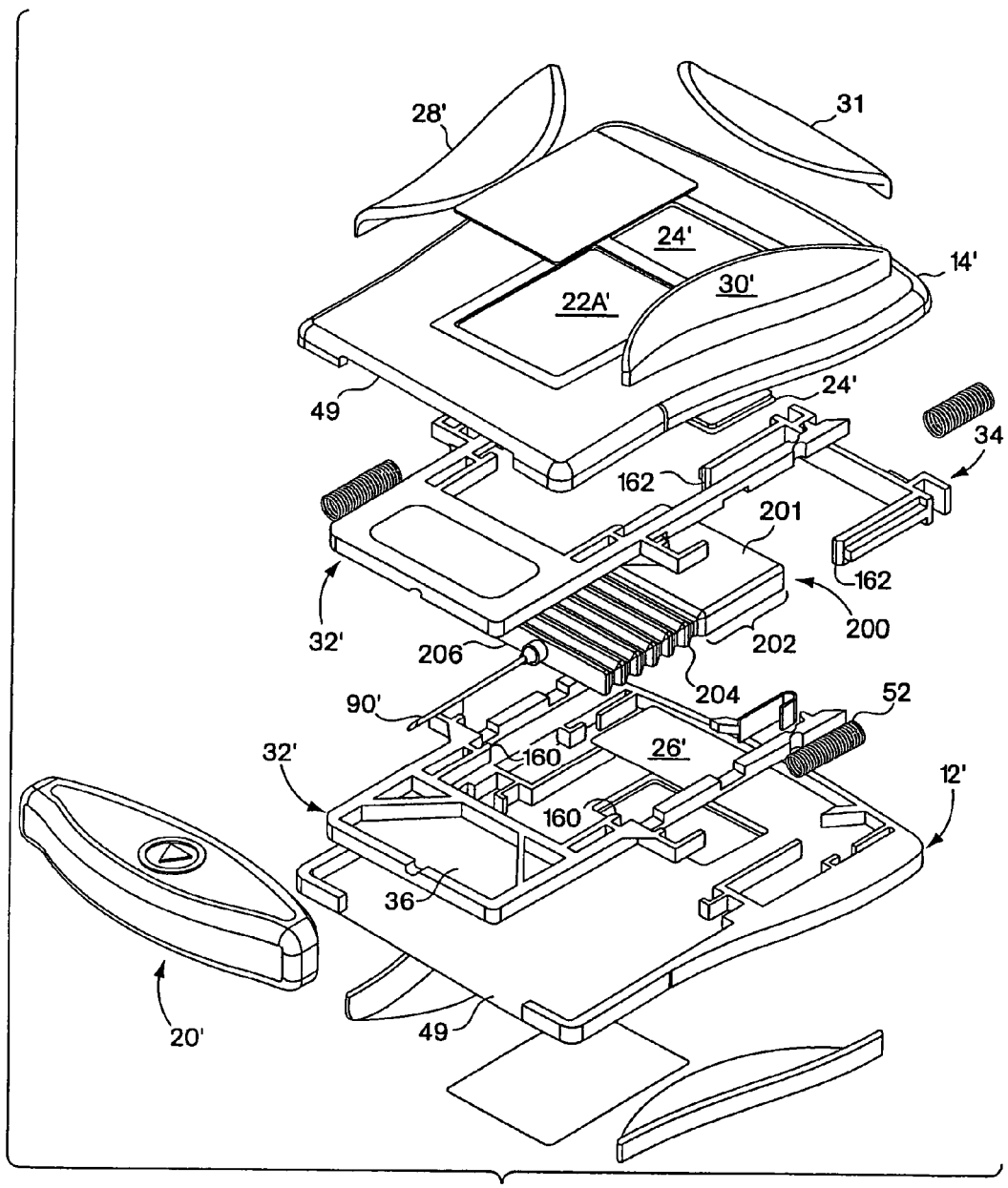
FIG. 24 is an exploded illustration of the components of the device shown in FIG. 23 illustrating use of a syringe in the form of a collapsible bellows.
Figure 26:
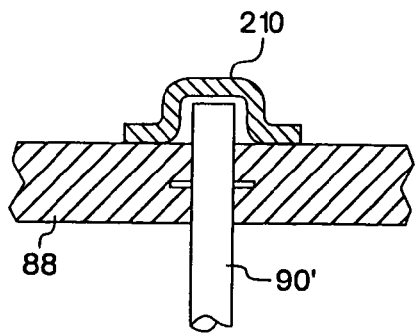
FIG. 26 is a diagrammatic illustration of a rupturable seal to isolate the contents of the bellows syringe of FIG. 25 from the needle.

FIGS. 17-22 illustrate the above-described device in various stages of operation. After the peel-away strip and cover 20 have been removed (FIG. 17) and the needle shield 36 of the actuator assembly 32 has been pressed against the patient's skin (FIG. 18), the syringe carrier will be released from its latched position to be driven distally under the influence of the drive spring 112 with sufficient force to cause the needle to pierce the skin and penetrate the tissue to the intended depth (FIG. 18). When the needle platform 120 abuts the surface 158, the sharp forward end of the needle will have penetrated the patient's tissue to the intended depth. The continued influence of the drive spring 146 drives the syringe carrier and the syringe, as a unit, forwardly, to cause the septum 112 to impale itself on the sharp rear end of the needle, communicating the lumen of the needle with the medication contained in the syringe. The supports 116 collapse until forward movement of the plunger 84 has terminated. The continued influence of the drive spring 146 will advance the syringe carrier and container 84 forwardly over the then-stationary plunger, collapsing the volume within the syringe and causing a bolus of the medicine to be injected into the patient (FIG. 26). Injection terminates when the compression of the syringe volume is terminated. As the injection stroke approaches its termination the arm locks 50 are tripped. With the actuator assembly arms 38 freed, the actuator assembly will advance forwardly relative to the housing under the influence of the side springs 52, as the device is withdrawn (FIG. 21). The needle shield 36 will be extended to cover and protect the forward end of the needle, with the arm latches 50 dropping into the rear apertures 170 to lock the actuator assembly 32 and needle shield 36 in the distally extended, needle protecting configuration (FIG. 22). With the needle shield extended in its distal, locked position, the biohazard indicia 166 on the flat faces of the shield are exposed prominently to serve their warning function.

It should be understood that the use of a compact, portable, pre-filled, single use auto-injector is not limited to administration of medicine for treatment of anaphylactic reaction. There are many medical conditions and circumstances that may make desirable a readily available, easily carried, injectable medication that may be administered by oneself or by another person without formal medical training. The medication to be injected may be one serving somewhat of an emergency function, such as administration of epinephrine, morphine, atropine, cardiotonic medication, anti-seizure medicines as for treatment of status epilepticus, antitoxins, anticoagulants and the like. Other medications deliverable by auto-injector may be more in the nature of convenience, such as administration of anti-migraine medication (e.g., sumatriptan or ergonovine), vaccines, growth hormone, antibiotics, injectable vitamins, and contraceptives, among others. Injectable medications may also include anticholinergic medication (atropine), anti-arrhythmics (e.g., lidocaine, amiodarome), drugs for the treatment of multiple sclerosis (e.g., interferon), cholinomimetics (e.g., neostigmine), anti-nausea and gastrointestinal stimulants (e.g., metoclopramide), diuretics (e.g., furosemide), sedatives and hynotics (e.g., hydroxyzine), anti-psychotic agents (e.g., haloperidol), analgesics (e.g., morphine), hypocalcimic drugs (e.g., calcitonin), corticosteroids (e.g., methyl prednisolone), anxiolytics (e.g., diazepam), insulin, erythropoietin, colony stimulating factor (e.g., Filgrastim), and anti-vertigo drugs (e.g., dimenhydrinate), anticoagulants (e.g., heparin and low-molecular-weight heparin), antidiuretic hormone, fusion inhibitors (e.g. T-20), monoclonal antibodies and interlukens. Other possible injectable medications will be apparent to those familiar with pharmaceuticals and the indications for their use.

FIGS. 23-29 illustrate another embodiment of the device in which the syringe includes walls that are collapsible in an accordion-like fashion. In this embodiment, the actuator assembly and syringe carrier may be considered as substantially the same as in the previously described embodiment. For convenience, elements in this embodiment that are identical to those in the previously described embodiment will be designated with the same reference numeral. In those instances where the device is essentially the same, but with slight modifications, either apparent from the drawing, or described, the reference numeral will be the same with a prime mark ('). For those components that warrant more detailed description, new reference numerals are used.

It may be noted that in this embodiment, the housing includes a peripheral configuration in which the rear portion is wider than the forward portion. It should be understood that although the previously described embodiment had a housing with peripheral dimensions approximating a rectangle, it may be desirable in some instances to configure the housing so that its rear end is wider or more narrow than its forward end. Indeed, the configuration of the housing may include non-rectangular peripheral geometries that, nonetheless, are flat and are containable within the defined flat virtual envelope.

Figure 25:
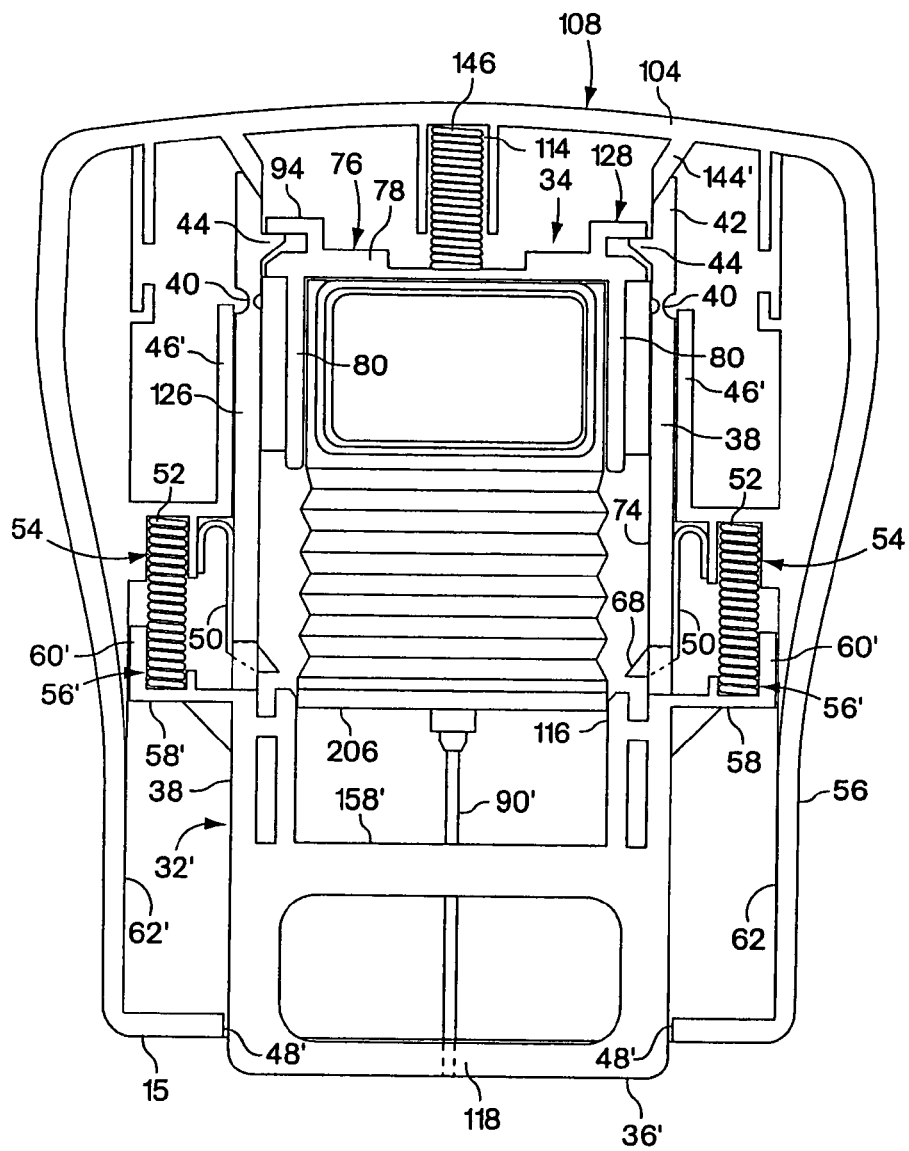
FIG. 25 is an illustration of the device of FIG. 24 with the front section of the housing removed and illustrating the configuration of the internal components in a retracted, storage configuration.

In this embodiment, the syringe 200 may be considered as having a relatively rigid, shape-retaining rear portion 202 adapted to fit securely within the generally rectangular opening defined by the U-shaped container carrier 76. The rearward portion 202 of the syringe 200 may be provided with a pair of windows 201, 203 on its front and rear surfaces, as by forming the syringe body from a transparent material such as polyethylene terephthalate (PET). The windows are located to be aligned with the windows 24', 26' on the front and rear housing sections 12', 14', when the device is in its retracted configuration (FIG. 25). The syringe may be formed, as by blow molding. The syringe body has a flat configuration, as defined.

The forward portion 204 of the syringe 200, in this exemplary embodiment, is collapsible and may be molded or otherwise formed in a collapsible bellows arrangement. The forward portions of the syringe 200 includes a sufficiently sturdy bottom wall 206 to provide a secure mount for a hypodermic needle 90'. The needle 208 extends longitudinally in a forward direction and terminates in a sharp tip. The medication is pre-loaded and sealed within the syringe body 200 when the device is fabricated so that it is not exposed to the lumen of the injection needle 208 until the device has begun its operation. To that end, a pressure rupturable membrane 210 may be disposed within the syringe 200 over the rear end of the needle 90' (FIG. 26). When, as described below, the pressure within the syringe 200 has increased to a sufficient predetermined level, the membrane 210 will rupture to immediately communicate the interior of the syringe 200 with the lumen of the injection needle 90'. It should be understood that other sealing arrangements may be employed, including arrangements in which the proximal end of the hypodermic needle pierces a sealing septum just before injection is to be completed as described in connection with the previous embodiment.

After the needle 90' has penetrated the tissue to the intended depth, the continued forwardly directed force of the injector spring 146 initiates longitudinal collapse of the syringe 200 and decrease of its internal volume. The rupturable membrane 210 that seals the container will burst when the pressure within the container has reached a predetermined design limit. When the membrane 210 ruptures, communication between the interior of the syringe and the lumen of the hypodermic needle 90 is established such that continued collapse of the syringe 200 under the influence of the injection spring 146 will force the liquid medication through the needle 90 into the patient. As with the previously described embodiment, the force of the injector spring 146 is selected to be sufficient to cause the desired volume of medication to be injected into the patient in a rapidly delivered bolus. Where the medication to be delivered is such, as with epinephrine, as to require a larger volume to be contained within the syringe, the extent to which the syringe 200 is compressed, can be limited by engagement of the forward end 162 of the syringe carrier 34 with the abutment surface 160 on the actuator assembly 32'.

Figure 27:
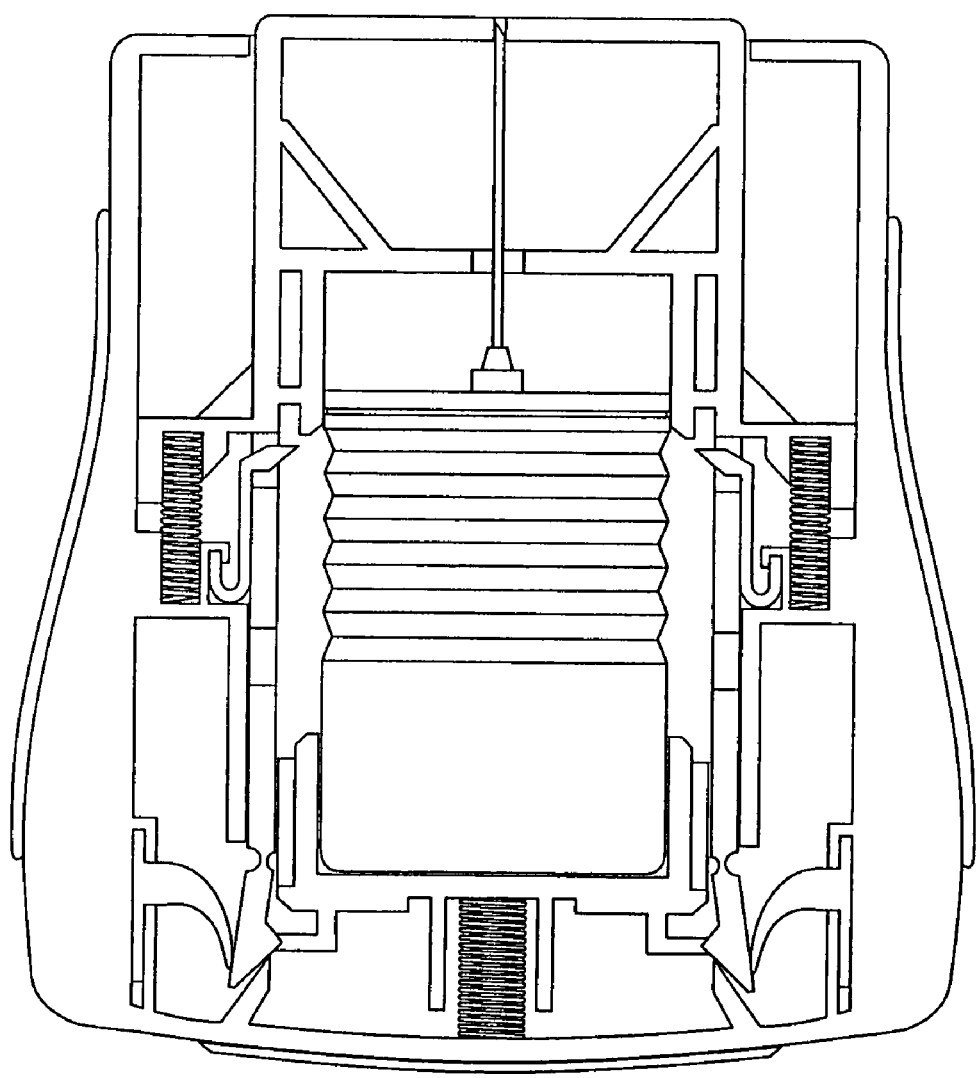
FIGS. 27-31 are sequential illustrations of the device in various stages of operation.
Figure 28:
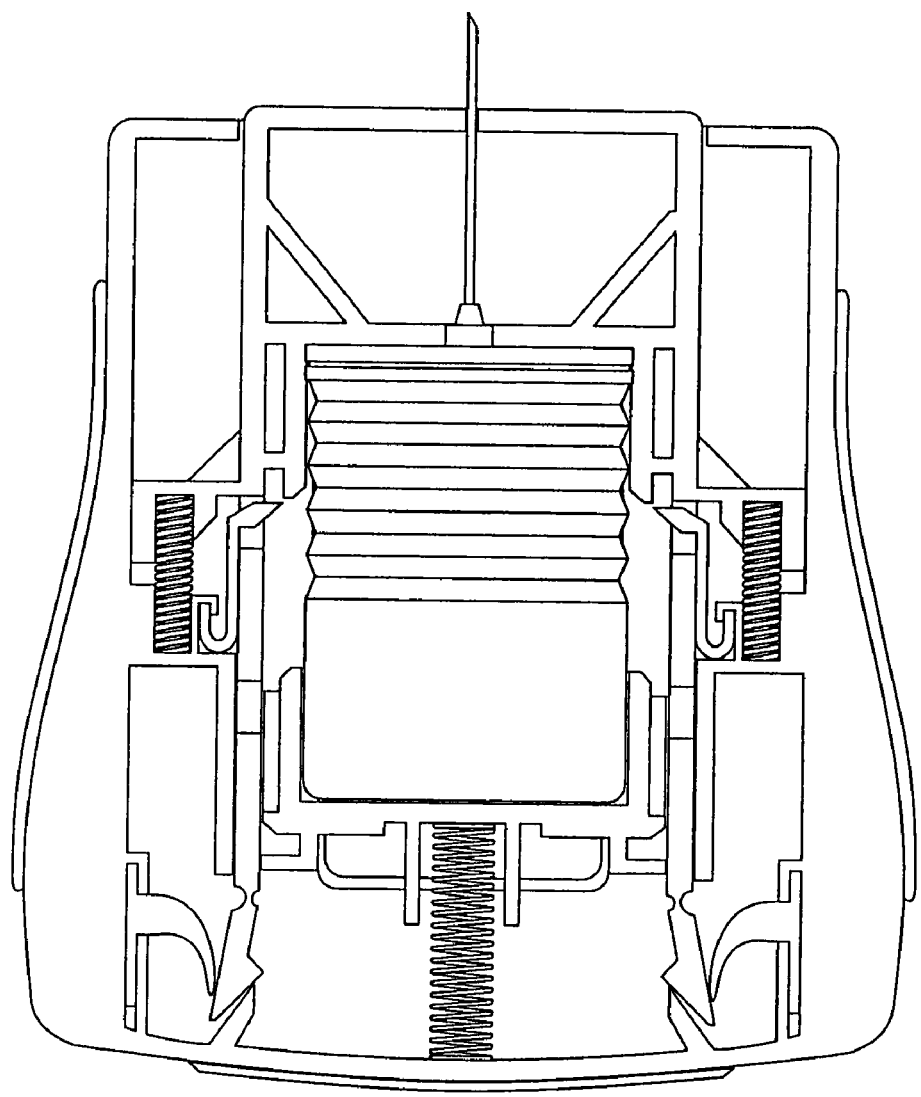
Figure 29:
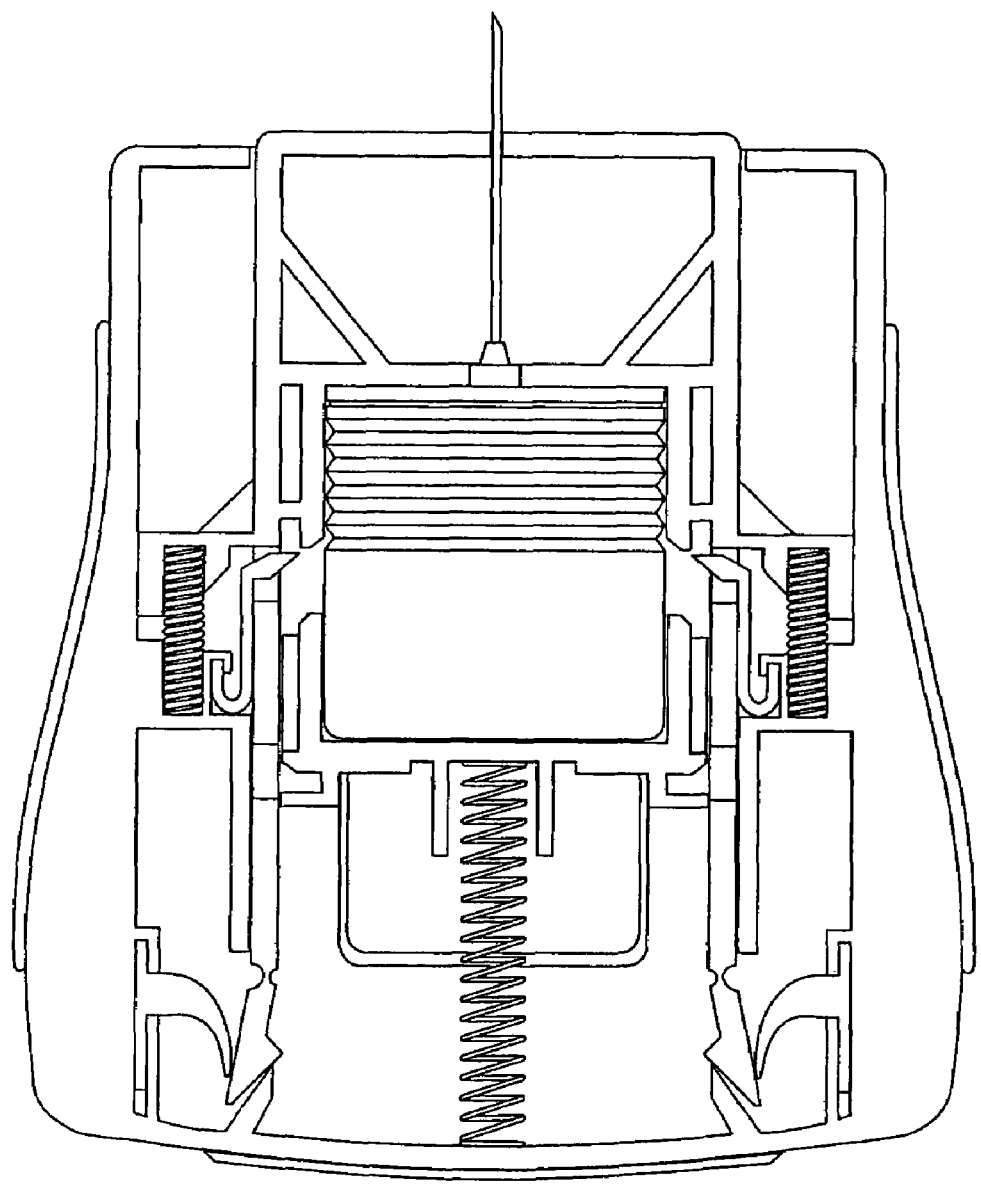
Figure 30:
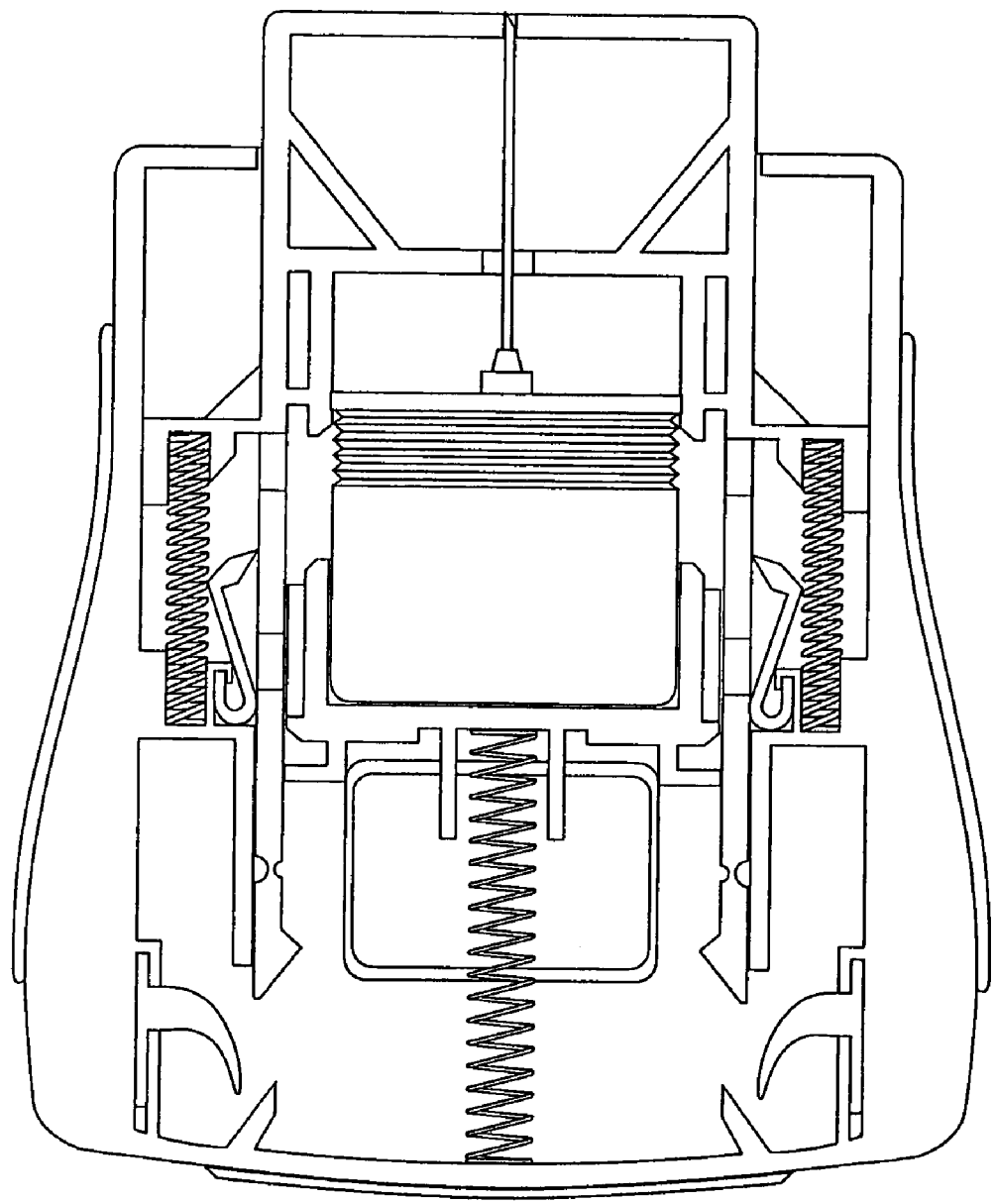
Figure 31:
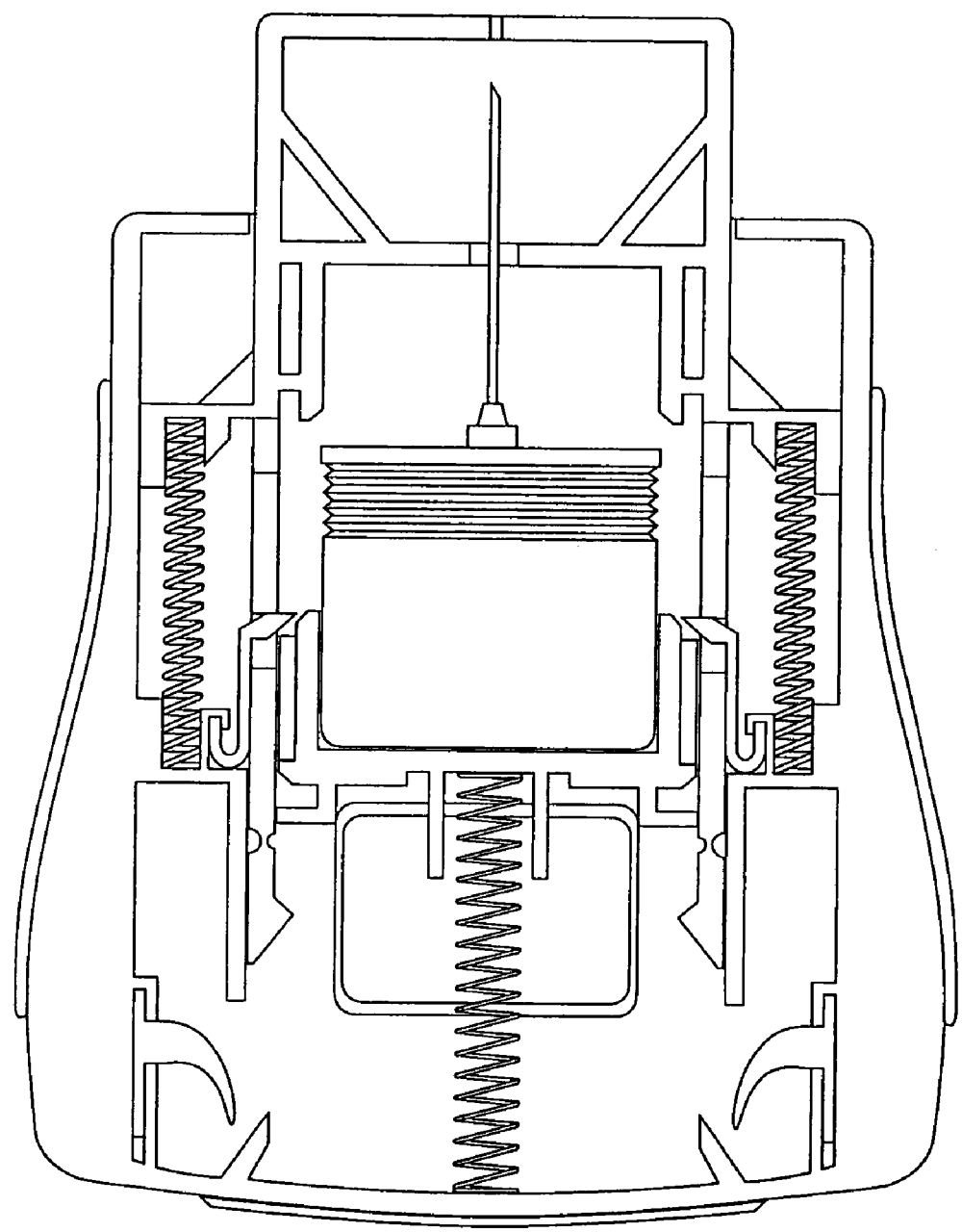

FIGS. 27-31 illustrate the above-described device in various stages of operation. FIG. 27 illustrates the device when it has been pressed against the patient's thigh to push the actuator assembly rearwardly into the housing 10 to an extent sufficient to release the latch 128' to initiate the needle penetration phase. FIG. 28 illustrates the components of the device when the injection spring 146 has advanced the syringe assembly distally to the point in which the forward end of the syringe body 200 (e.g., the bottom wall 206 of the bellows in this embodiment) is advanced into engagement with the abutment surface 158' of the actuator assembly. At this point, the needle 208 will have been projected beyond the forward end 156' of the needle shield 36' and will have penetrated into the patient's tissue to the predetermined depth and the injector spring 146 and syringe carrier will continue to advance to the stage illustrated in FIG. 29. During the advancement to the FIG. 29 stage, the bellows 204 is compressed, first causing a build-up of pressure within the syringe body sufficient to effect communication with the lumen of the needle 208 and then to forcefully inject the bolus of medication through the needle and into the patient. As the injection progresses under the influence of the injection spring 146, the forward ends of the syringe carrier engages the finger 68 of the latches 50 to urge the latches outwardly, disengaging the fingers from the arms. FIG. 30 illustrates the device after the injection phase has been completed, with the latches 50 having been tripped. When the latches 50 disengage from the arms, the actuator assembly 34 is released and is driven forwardly by the springs 52, causing the rearward portion of the needle shield 36' to project beyond the forward end of the housing. The forward end 156' of the needle shield is maintained in contact with the patient's skin throughout that motion so that the shield progressively covers the needle 208 as the housing 10' is drawn away from the skin. That motion continues until the device has reached the stage as shown in FIG. 31 in which the needle shield 36' has extended fully to completely cover and protect the needle 208. At this stage, the actuator assembly will have advanced forwardly relative to the housing to the point where the latches 50 snap into engagement with the rear sockets 126 on the arms 38. With the latches so re-engaged, the actuator assembly is locked in a position in which the needle shield cannot be urged back into the housing. In this configuration, the rear portion of the shield on which a label bearing the biohazard icon will be exposed, indicating that the device has been used and that it contains a biohazard sharp.

From the foregoing, it will be appreciated that the various aspects and features disclosed may be used in varying combinations, depending on the specifics of the intended application, the medication and the circumstances in which it can be expected to be injected. Among the features described are an auto-injector having a flat housing; an auto-injector having a broad flat surface with easily understood pictograms of sufficient size to enhance immediate understanding of the manner of use of the device; an auto-injector for rapid bolus delivery having a flat housing dimensioned to be less bulky and easily carried on one's person; a needle shield for an auto-injector that is of a generally flat configuration to present a broad face adapted to carry a label with indicia evident of a biohazard; an auto-injector with a housing having elastomeric grips embedded with a material to cause the grips to glow in a darkened environment; an auto-injector in which the injection needle and actuation member are located at the same end of the housing of the device and where the actuator also serves as a needle guide and a needle shield; an auto-injector in which the needle is concealed at all times, including before, during or after use; an inherently safe three step method for using an auto-injector that includes breaking a seal, removing a cover and applying the injector to the injection site; as well as all other features described in this specification.

Although the following claims represent what we desire to claim as of the filing date of this application, it should be understood that further claims may be added and that the scope of the claims may be broadened as the prosecution of this application, or any application which relies for priority on this application, progresses.

We claim:

1. A method for automatically administering injectable medication comprising:
   storing the medication in a flat syringe having an injection needle;
   enclosing the flat syringe within a separate flat housing that includes a self-contained power source and drive mechanism for driving the syringe from a storage configuration in which the syringe and needle are contained completely within the housing to an injection configuration in which the injection needle protrudes from a region of the housing;
   providing an actuator movably mounted to the housing at said region of the housing, the actuator being operatively associated with the drive mechanism to release the syringe for movement to the injection position in response to movement of the actuator relative to the housing by urging of the actuator against an injection site;
   providing a cover on said region of the housing to completely enclose the region of the housing from which the needle and actuator extend, the method further comprising:
   removing the cover from the housing and pressing the actuator against the injection site and under a force sufficient to cause release of the syringe to enable the self-contained power source and drive mechanism to drive the syringe to an injection configuration.

2. A method for rapid automatic self-administration of a bolus of injectable medication comprising:
   providing a flat housing having forward and rearward ends with a separate flat syringe contained within the housing, the syringe containing an injectable medication; a needle, extendable from a position contained completely within the housing to an injection position projecting beyond the forward end of the housing; an actuating member movably mounted to the housing and extending beyond the forward end of the housing; the housing containing powered mechanisms to extend the needle to the injection position and operate the syringe to inject a bolus of medication; a cover attached to the forward end of the housing and enclosing the forward end of the housing;
   the method further comprising:
   grasping the rear end of the housing in one hand and, while so holding the housing, removing the cover with the other hand to expose the forward end of the housing and the actuator; and
   then pressing the actuating member firmly against the intended injection site under a force sufficient to trigger the mechanisms for extending the needle and operating the syringe.

3. A method as defined in claim 2 further comprising:
   preliminarily providing a peel-away strip connecting the cover to the housing and, before removal of the cover, peeling away the peel-away strip to facilitate cover removal.

4. An auto-injector comprising:
   a flat housing having a forward end;
   a flat container in the housing for storing an injectable medication;
   an injection needle having a sharp forward end, the needle being connectible with the interior of the container to enable medication to flow to and through the needle; and
   a needle shield extendable from the forward end of the housing, the needle shield being substantially flat and having a needle-receptive passageway formed therethrough;
   the needle shield being automatically extendable, upon disengagement from an injection site, from a retracted position to an extended position, the extended position being sufficiently forward of the housing to cover the extended needle; and
   a biohazard indicator on at least one flat surface of the needle shield.

5. An auto-injector as defined in claim 4 wherein the biohazard indicator is concealed within the housing when the needle shield is retracted and is exposed when the needle shield is in its fully extended position.

* * * * *